United States Patent
Perez

(10) Patent No.: US 7,497,866 B2
(45) Date of Patent: Mar. 3, 2009

(54) METHODS FOR PRODUCING EPITHELIAL FLAPS ON THE CORNEA AND FOR PLACEMENT OF OCULAR DEVICES AND LENSES BENEATH AN EPITHELIAL FLAP OR MEMBRANE, EPITHELIAL DELAMINATING DEVICES, AND STRUCTURES OF EPITHELIUM AND OCULAR DEVICES AND LENSES

(75) Inventor: Edward Perez, Redwood City, CA (US)

(73) Assignee: Tissue Engineering Refraction Inc., Palo Alto, CA (US)

( * ) Notice: Subject to any disclaimer, the term of this patent is extended or adjusted under 35 U.S.C. 154(b) by 683 days.

(21) Appl. No.: 10/346,664

(22) Filed: Jan. 17, 2003

(65) Prior Publication Data

US 2003/0220653 A1 Nov. 27, 2003

Related U.S. Application Data

(63) Continuation-in-part of application No. PCT/US01/22633, filed on Jul. 18, 2001, and a continuation-in-part of application No. 09/618,580, filed on Jul. 18, 2000, now Pat. No. 6,544,286.

(60) Provisional application No. 60/408,226, filed on Sep. 3, 2002, provisional application No. 60/393,305, filed on Jul. 1, 2002, provisional application No. 60/350,003, filed on Jan. 17, 2002.

(51) Int. Cl.
*A61F 9/00* (2006.01)
(52) U.S. Cl. ...................................... 606/166; 623/6.12
(58) Field of Classification Search ................. 606/4–6, 606/107, 166
See application file for complete search history.

(56) References Cited

U.S. PATENT DOCUMENTS 4,346,482 A 8/1982 Tennant et al.

(Continued)

FOREIGN PATENT DOCUMENTS

| WO | WO 02/06883 | 1/2002 |
|----|-------------|--------|
| WO | WO 03/009789 | 2/2003 |

OTHER PUBLICATIONS

International Search Report mailed Apr. 22, 2004, for PCT patent application No. PCT/US03/01549, filed on Jan. 17, 2003, 6 pages.

(Continued)

*Primary Examiner*—Kevin T Truong
*Assistant Examiner*—Victor X Nguyen
(74) *Attorney, Agent, or Firm*—Wheelock Chan LLP; E. Thomas Wheelock

(57) ABSTRACT

These methods, devices, and structures are useful in the field of ophthalmology; the devices and methods relate variously to separating or lifting corneal epithelium from the eye preferably in a substantially continuous layer, placing a lens or other suitable ocular or medical device beneath the epithelial membrane, and to the resulting structures formed by those procedures. The de-epilthelialization devices generally utilize a non-cutting separator or dissector that is configured to separate the epithelium at a naturally occurring cleavage surface in the eye between the epithelium and the corneal stroma (Bowman's membrane), specifically separating in the region of the lamina lucida. The separator or dissector may have a structure that rolls or vibrates (or both) at that cleavage surface or interface during the dissection step. The separated epithelium may be lifted or peeled from the surface of the eye to form an epithelial flap or a pocket. The epithelium may then be replaced on the cornea after a refractive procedure or after placement of an ocular lens (or other subepithelial device) on the eye. The subepithelial device may comprise a wide variety of synthetic, natural, or composite polymeric materials. The step of replacing epithelial tissue upon the subepithelial device or upon the anterior corneal surface promotes epithelial healing.

82 Claims, 23 Drawing Sheets

U.S. PATENT DOCUMENTS

| | | | |
|---|---|---|---|
| 4,440,918 A | 4/1984 | Rice et al. | |
| 4,607,617 A | 8/1986 | Choyce | |
| 4,646,720 A | 3/1987 | Peyman et al. | |
| 4,662,881 A | 5/1987 | Nordan | |
| 4,676,790 A | 6/1987 | Kern | |
| 4,693,715 A | 9/1987 | Abel, Jr. | |
| 4,715,858 A | 12/1987 | Lindstrom | |
| 4,793,344 A | 12/1988 | Cumming et al. | |
| 4,818,801 A | 4/1989 | Rice et al. | |
| 5,057,578 A | 10/1991 | Spinelli | |
| 5,171,318 A | 12/1992 | Gibson et al. | |
| 5,192,316 A | 3/1993 | Ting | |
| 5,213,720 A | 5/1993 | Civerchia | |
| 5,300,116 A | 4/1994 | Chirila et al. | |
| 5,312,330 A * | 5/1994 | Klopotek | 604/521 |
| 5,314,960 A | 5/1994 | Spinelli et al. | |
| 5,371,147 A | 12/1994 | Spinelli et al. | |
| 5,374,515 A | 12/1994 | Parenteau et al. | |
| 5,395,385 A | 3/1995 | Kilmer et al. | |
| 5,458,819 A | 10/1995 | Chirila et al. | |
| 5,496,339 A | 3/1996 | Koepnick | |
| 5,522,888 A | 6/1996 | Civerchia | |
| 5,599,341 A * | 2/1997 | Mathis et al. | 606/5 |
| 5,632,773 A | 5/1997 | Graham et al. | |
| 5,634,921 A * | 6/1997 | Hood et al. | 606/5 |
| 5,713,957 A | 2/1998 | Steele et al. | |
| 5,716,633 A | 2/1998 | Civerchia | |
| 5,777,719 A | 7/1998 | Williams et al. | |
| 5,786,434 A | 7/1998 | Ando et al. | |
| 5,827,641 A | 10/1998 | Parenteau et al. | |
| 5,919,185 A | 7/1999 | Peyman | |
| 5,994,133 A | 11/1999 | Meijs et al. | |
| 6,030,398 A | 2/2000 | Klopotek | |
| 6,036,683 A | 3/2000 | Jean et al. | |
| 6,099,541 A | 8/2000 | Klopotek | |
| 6,126,668 A * | 10/2000 | Bair et al. | 606/166 |
| 6,176,580 B1 | 1/2001 | Roffman et al. | |
| 6,187,053 B1 | 2/2001 | Minuth | |
| 6,225,367 B1 | 5/2001 | Chaouk et al. | |
| 6,228,113 B1 | 5/2001 | Kaufman | |
| 6,231,583 B1 * | 5/2001 | Lee | 606/166 |
| 6,280,435 B1 | 8/2001 | Odrich et al. | |
| 6,280,469 B1 | 8/2001 | Terry et al. | |
| 6,391,055 B1 | 5/2002 | Ikada et al. | |
| 2003/0018347 A1 | 1/2003 | Pallikaris et al. | |
| 2003/0018348 A1 | 1/2003 | Pallikaris et al. | |
| 2003/0083743 A1 | 5/2003 | Perez | |
| 2003/0105521 A1 | 6/2003 | Perez | |

OTHER PUBLICATIONS

Azar, D. T. et al. (2001). "Laxer Subepithelial Keratomileusis: Electron Microscopy and Visual Outcomes of Flap Photorefractive Keratectomy," *Current Opinion in Ophathalmology*, 12: 323-328.

Beerens, E. G. J. et al. (1975). "Rapid Regeneration of the Dermal-Epidermal Junction After Partial Separation by Vacuum: An Electron Microscopic Study," *The Journal of Investigative Dermatology* 65(6):513-521.

Chen, K-H. et al. (2001). "Transplantation of Adult Human Corneal Endothelium Ex Vivo: A Morphologic Study," *Cornea* 20(7):731-737.

Green, K. J. et al. (1996). "Desmosomes and Hemidesmosomes: Structure and Function of Molecular Components," *FASEB J* 10:871-881.

Joo, C-K et al. (2000). "Repopulation of Denuded Murine Descemet's Membrane with Life-Extended Murine Corneal Endothelial Cells as a Model for Corneal Cell Transplantation," *Graefes Archive for Clinical and Experimental Ophthalmology* 238(2):174-180.

Katz, S. I. (1984). "The Epidermal Basement Membrane: Structure, Onlogeny and Role in Disease, " *In Basement Membranes and Cell Movement* Pitman: London Ciba Foundation Symposium No. 108, pp. 243-259.

Kiistala, U. (1972), "Dermal-Epidermal Separation, II, External Factors in Suction Blister Formation with Special Reference to the Effect of Temperature," *Annal of Clinical Research* 4:236-246.

Schwab, I. R. and Isseroff, R. R., (2000). "Bioenginered Corneas - The Promise and the Challenge," *New England Journal of Medicine* 343(2):136-138.

Tsai, R.J.-F. et al. (2000). "Reconstruction of Damaged Corneas by Transplantation of Autologous Limbal Epithelial Cells" *New England Journal of Medicine* 343(2):86-93.

van der Leun, J. C. et al. (1974). "Repair of Dermal-Epidermal Adherence: A Rapid Process Observed in Experiments on Blistering with Interrupted Suction," *The Journal of Investigative Dermatology* 63(5):397-401.

Willsteed, E.M. et al. (1991). "An Ultrastructural Comparison of Dermo-Epidermal Separation Techniques," *J Curan Pathol* 18:8-12.

* cited by examiner

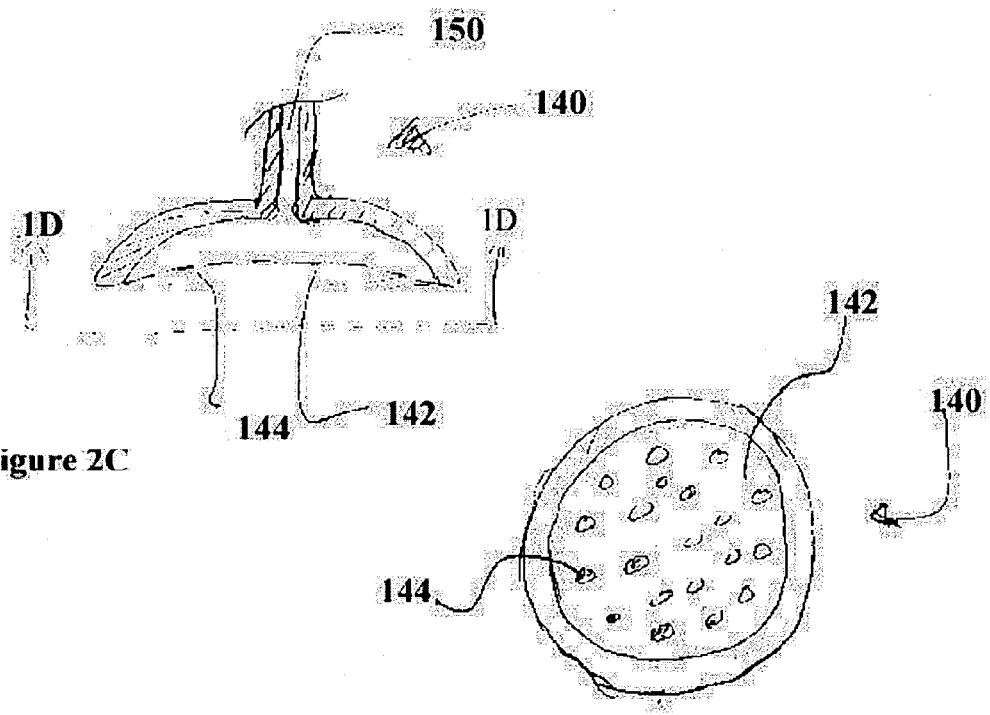
Figure 2C
Figure 2D
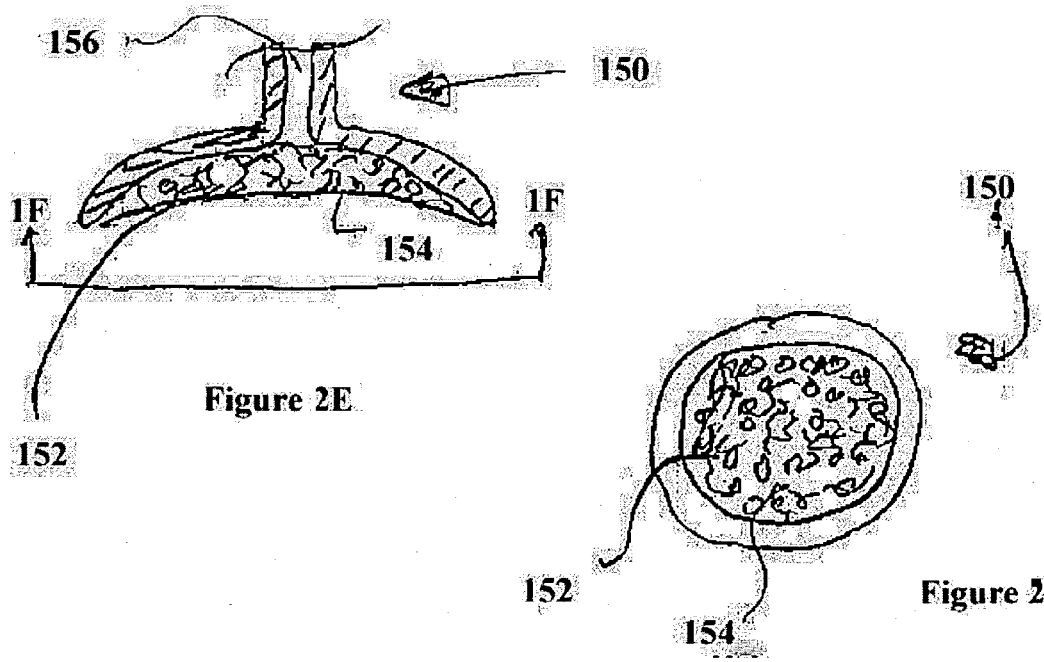
Figure 2E
Figure 2F

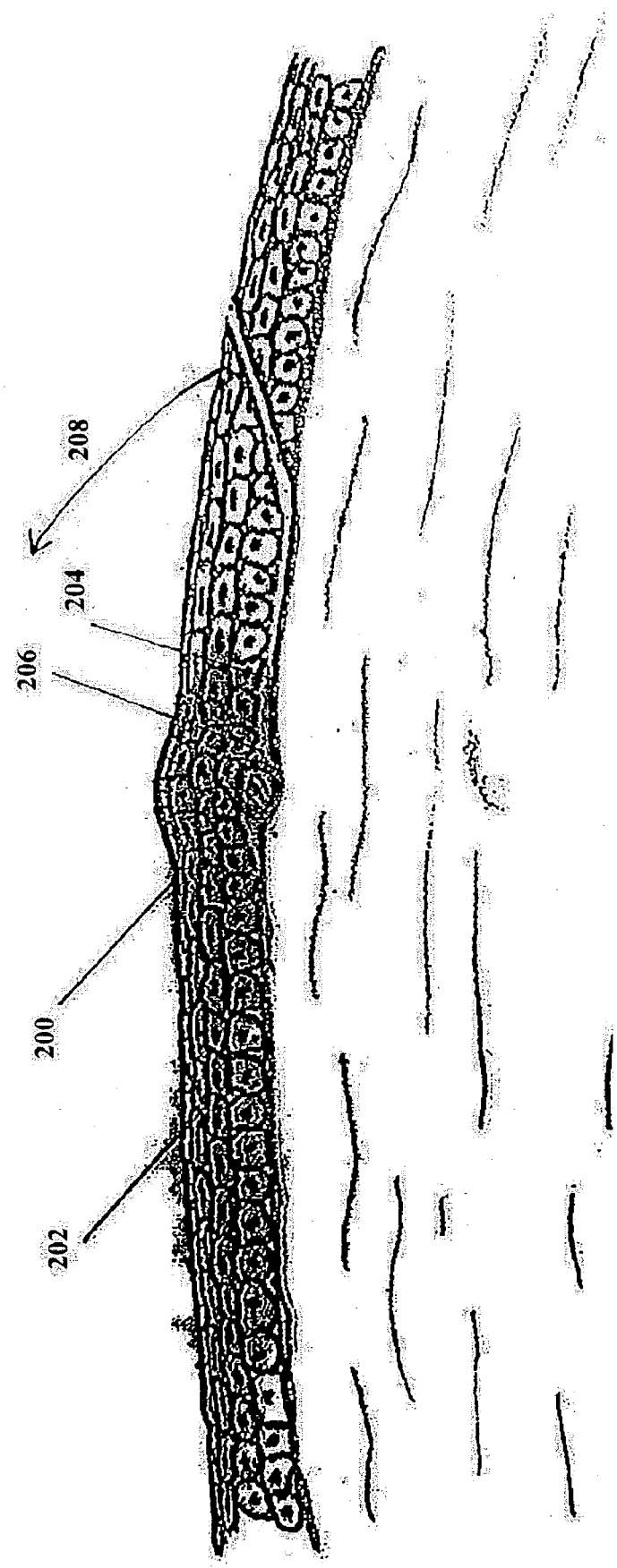

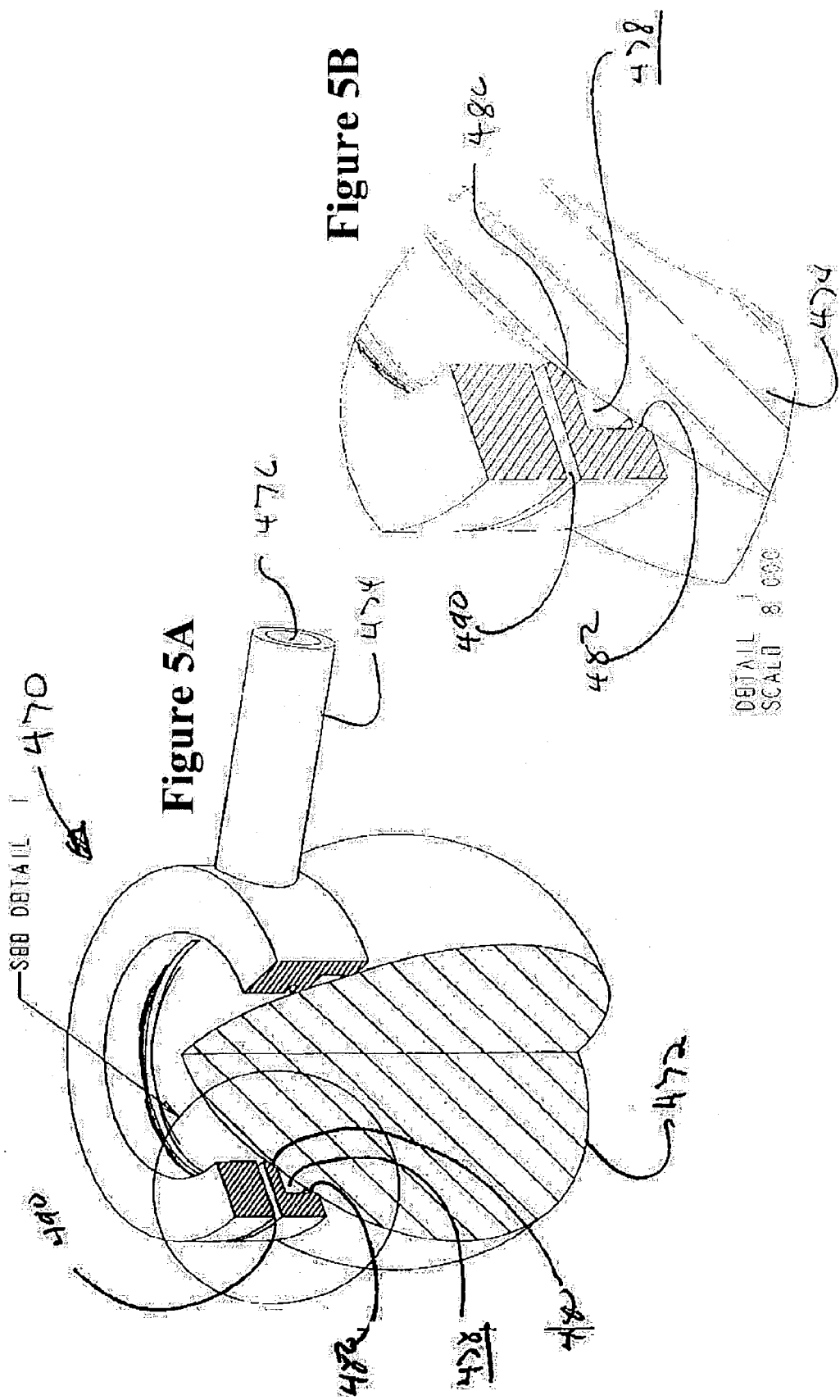

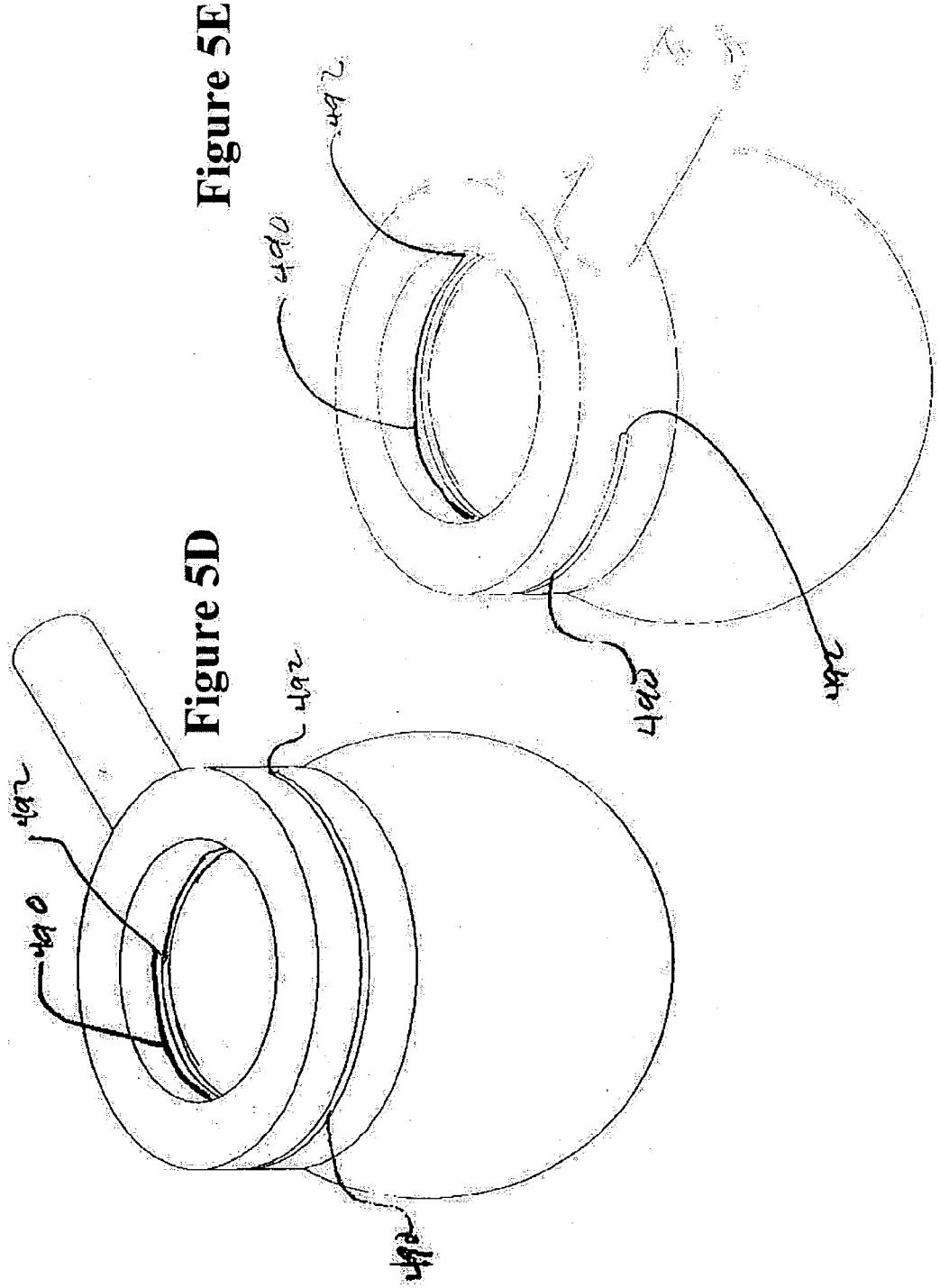

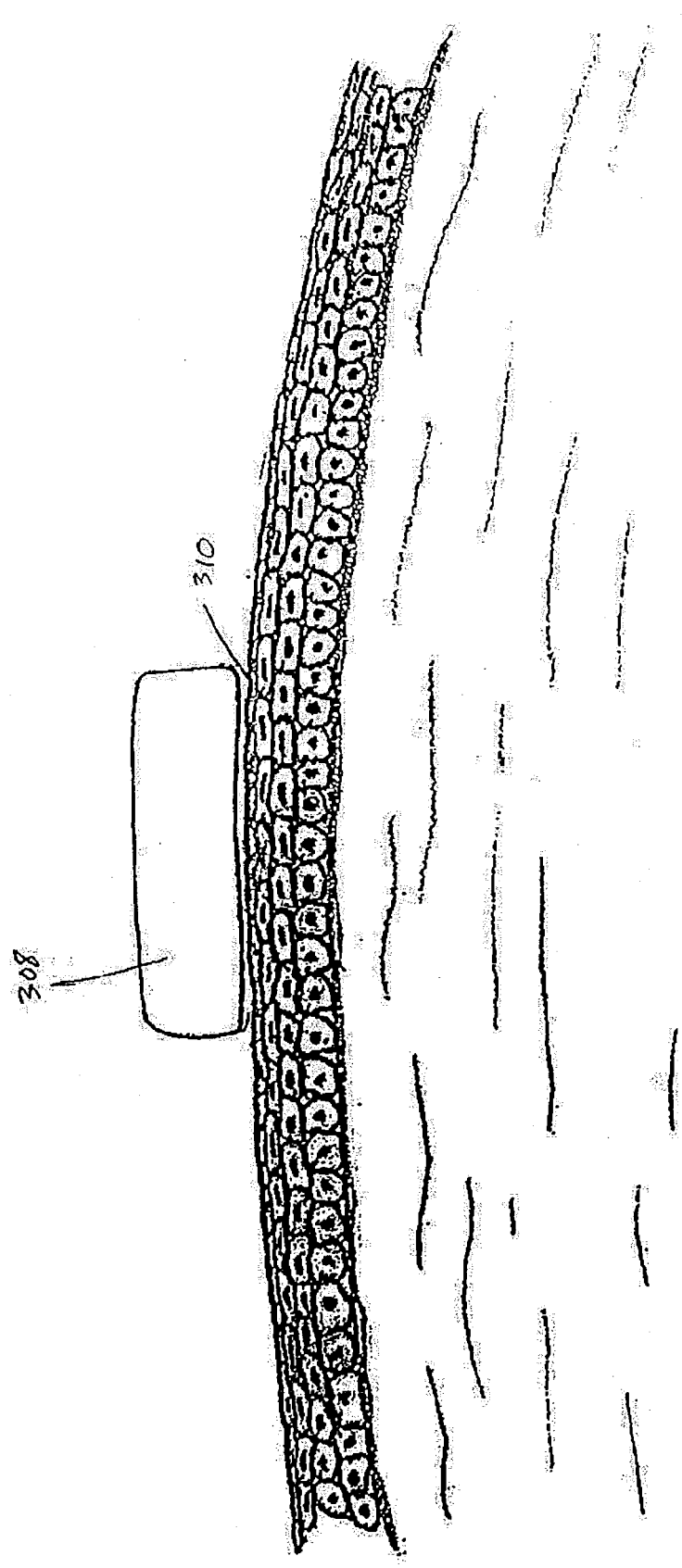

METHODS FOR PRODUCING EPITHELIAL FLAPS ON THE CORNEA AND FOR PLACEMENT OF OCULAR DEVICES AND LENSES BENEATH AN EPITHELIAL FLAP OR MEMBRANE, EPITHELIAL DELAMINATING DEVICES, AND STRUCTURES OF EPITHELIUM AND OCULAR DEVICES AND LENSES

RELATED APPLICATIONS

This is a continuation-in-part of PCT Application No. PCT/US01/22633, having an International Filing Date of Jul. 18, 2001 and a continuation-in-part of pending U.S. patent application Ser. No. 09/618,580, filed Jul. 18, 2000 and derives benefit under 35 USC 119 from each of U.S. Provisional Application No. 60/350,003 entitled "EPITHELIAL DELAMINATING DEVICE" filed Jan. 17, 2002; U.S. Provisional Application Ser. No. 60/393,305 entitled "EPITHELIAL DELAMINATING DEVICE (II)" filed Jul. 1, 2002; and U.S. Provisional Application Ser. No. 60/408,226 entitled "EPITHELIAL DELAMINATING DEVICE (III)" filed Oct. 3, 2002, each of which are specifically incorporated in their entirety by reference.

FIELD OF THE INVENTION

This invention is in the field of ophthalmology. It relates variously to devices and methods for separating or lifting corneal epithelium from the eye preferably in a substantially continuous layer, placing a lens or other suitable ocular or medical device beneath the epithelial membrane, and to the resulting structures formed by those procedures. The de-epithelialization devices generally utilize a non-cutting separator or dissector that is configured to separate the epithelium at a naturally occurring cleavage surface in the eye between the epithelium and the corneal stroma (Bowman's membrane), specifically separating in the region of the lamina lucida. The separator or dissector may have a structure that rolls or vibrates (or both) at that cleavage surface or interface during the dissection step. The separated epithelium may be lifted or peeled from the surface of the eye to form an epithelial flap or a pocket. The epithelium may then be replaced on the cornea after a refractive procedure or after placement of an ocular lens (or other subepithelial device) on the eye. The subepithelial device may comprise a wide variety of synthetic, natural, or composite polymeric materials. The step of replacing epithelial tissue upon the subepithelial device or upon the anterior corneal surface promotes epithelial healing.

BACKGROUND OF THE INVENTION

Refractive surgery refers to a set of surgical procedures that change the native optical or focusing power of the eye. These changes alleviate the need for glasses or contact lenses that an individual might otherwise be dependent on for clear sight. The majority of the focusing power in the human eye is dictated by the curvature of the air-liquid interface, where there is the greatest change in the index of refraction. This curved interface is the outer surface of the cornea. The refractive power of this interface accounts for approximately 70% of the total magnification of the eye. Light rays that make up the images we see pass through the cornea, the anterior chamber, the crystalline lens, and the vitreous humor before they are focused on the retina to form an image. It is the magnifying power of this curved, air-corneal interface that provided the field of refractive surgery with the opportunity to surgically correct visual deficiencies.

Initial refractive surgical procedures corrected nearsightedness by flattening of the curvature of the cornea. The first largely successful procedure was called radial keratotomy (RK). RK was widely used during the 1970's and early 1980's where radially oriented incisions were made in the periphery of the cornea. These incisions allowed the peripheral cornea to bow outwards, consequently flattening the central optical zone of the cornea. This was fairly easy and thus, popular, but it rarely did more than lessen one's dependency on glasses or contract lenses.

A largely flawed and failed procedure called epikeratophakia was developed in the era of RK. It is now essentially an academic anomaly. Epikeratophakia provided a new curvature to the outer curvature of the cornea by grafting onto the cornea a thin layer of preserved corneal tissue. Lyophilization is the preservation method used in epikeratophakia where the cornea is freeze-dried. The tissue is not acellularized but is rendered non-living. During the process of freeze drying, the cornea is also ground to a specific curvature.

The epikeratophakia lens was placed into the eye surgically. An annular 360° incision was placed into the cornea after completely removing the epithelium from where the epikeratophakic lens would sit. The perimeter of this lens would be inserted into the annular incision and held in place by a running suture. There were several problems with epikeratophakia: 1) the lenses remained cloudy until host stromal fibroblasts colonized the lens, which colonization possibly could take several months; 2) until migrating epithelium could grow over the incision site onto the surface of the lens, the interrupted epithelium was a nidus for infection; and 3) epithelium healing onto the surgical site sometimes moved into the space between the lens and the host cornea. Currently, epikeratophakia is limited in its use. It is now used in pediatric aphakic patients who are unable to tolerate very steep contact lenses.

Major industrial research efforts tried to produce a synthetic version of the epikeratophakic graft called the synthetic onlay in a synthetic epilens. Development of synthetic epikeratophakia was undertaken in order to make a viable refractive product (i.e. adequate raw materials for mass production and quality control for operations). Different synthetic polymers were used (hydroxyethylmethacrylate, polyethylene oxide, lidofilcon, polyvinyl alcohol). Hydrogels of these materials normally did not have a surface that was readily conducive to epithelial cells growing and adhering onto these synthetic surfaces. This was one of the major setbacks of synthetic onlays. Epithelial cells could not adequately heal onto these lenses. The success of any epikeratophakia procedure is dependent on epithelial wound healing and epithelial coverage over the surface not covered by the epithelium, typically at least the implant surface.

Another problem with those previous synthetic lenses is that they did not adhere well to the surface of the eye. Conventional suturing was difficult and the use of biological glues was also flawed. Glues were not ideally biocompatible in the cornea.

Lastly, the permeability of these hydrogels was significantly limiting. Living epithelial cells on the surface had difficulty achieving adequate nutrition. Corneal epithelial nutritional flow is from the aqueous humor through the cornea out to the epithelial cells. In the end, industrial efforts failed to develop an adequate synthetic epikeratophakic lens.

Around the mid-1990's, procedures that sculpt the cornea with lasers were sufficiently successful that they began to replace radial keratotomy. The first generation of laser ablation of the cornea was called photorefractive keratectomy (PRK). In PRK, an ablative laser (e.g., an excimer laser) is focused on the cornea to sculpt a new curvature into the surface. In PRK, the epithelium is destroyed when achieving a new outer surface curve. Over the ensuing post-operative days, the epithelium has to grow or heal back into place. This epithelial healing phase was problematic for most patients since the epithelially denuded and ablated cornea was painful. It is also initially difficult to see, and this "recuperative time" can last from days to a week or more.

A subsequent variation of PRK corneal laser ablation, LASIK, has become very popular. The LASIK procedure, also known as LASer In situ Keratomileusis (LASEK), is synonymous in the public mind with laser vision correction. In LASIK, an outer portion (or chord-like lens-shaped portion) of the cornea (80 to 150 microns thick) is surgically cut from the corneal surface. This is performed by a device called a microkeratome. The microkeratome is a device which cuts a circular flap from the surface of the cornea that remains hinged at one edge. This flap is reflected back and an ablative (excimer) laser is used to remove or to reform a portion of the exposed surgical bed. The flap is laid back into place. When this flap is laid back into place, the cornea achieves a new curvature because the flap conforms to the laser-modified surface. In this procedure, epithelial cells are not removed or harmed. The epithelial cells have simply been incised at the edge of this flap. When the flap is placed back onto the corneal bed, the epithelium heals back at the incision site. There is essentially no recuperative time and the results are almost immediate. Because there is very little surgical time (15 minutes for each eye) and because there are lasting and very accurate results, LASIK is currently considered the premier manner of performing refractive surgery.

The newest technique being evaluated in high volume refractive surgical practices and in some academic centers is a procedure called Laser Assisted Subepithelial Keratomileusis (LASEK). In LASEK, a "flap" is made of only epithelium. This layer of epithelium is lifted off the cornea in a manner similar to LASIK. The ablative laser is focused just on the surface of the denuded cornea (in the same manner as was done with PRK). However, this epithelial flap is left intact, i.e., epithelium is not destroyed. It is simply rolled back into place after formation of the re-curved anterior portion of the cornea, resulting in much less recuperative time than with PRK. Current methods of LASEK are not as good as LASIK but the results are better than with PRK.

The corneal epithelium is a multilayered epithelial structure typically about 50 µm in thickness. It is non-cornified. The outer cells are living, although they are squamous in nature. The basal epithelial cells are cuboidal and sit on the stromal surface on a structure known as Bowman's membrane. The basal cell layers is typically about 1 mil thick (0.001"). The basal cells produce the same keratins that are produced in the integument, i.e., skin. The basal epithelial cells express keratins 5 and 14 and have the potential to differentiate into the squamous epithelial cells of the corneal epithelium that produce keratins 6 and 9. The corneal epithelium has a number of important properties: 1) it is clear; 2) it is impermeable; 3) it is a barrier to external agents; and 4) it is a highly innervated organ. Nerves from the cornea directly feed into the epithelium, and thus, defects of this organ produce pain.

Epithelial cells are attached side-to-side by transmembrane molecules called desmosomes. Another transmembrane protein, the hemidesmosome, connects to collagen type 7 and is present on the basolateral surface of basal epithelial cells. Hemidesmosomes anchor epithelium to the underlying collagenous portion of the stroma. The junction between the epithelium and corneal stroma is referred to as basement membrane zone (BMZ).

When LASEK is performed, a physical well is placed or formed on the epithelium and filled with a selection of 20 percent ethanol and balanced salt solution. Contact with the solution causes the epithelial cells to lose their adherence at the BMZ, most likely by destroying a portion of that cell population. The epithelium is then raised by pushing the epithelium, e.g., with a Weck sponge, in a manner similar to striping a wall of paint. The exposed collagenous portion of the corneal stroma is then ablated to reshape its surface. A weakened epithelium is then rolled back into place to serve as a bandage. However, this "bandage" fails to restore the epithelium to its original state, i.e., it does not preserve the integrity of the epithelium, thereby reducing its clarity, impermeability to water, and barrier function. Furthermore, the ability of the epithelium to adhere to the corneal stromal surface is impaired.

U.S. Pat. Nos. 6,099,541 and 6,030,398 to Klopotek describe an microkeratome apparatus and method for cutting a layer of corneal epithelium to prepare the eye for LASIK or other reshaping procedures. The epithelium, if replaced, is attached using surgical techniques.

None of the cited references shows or suggests my invention as described herein.

REFERENCES

Kiistala, U. (1972). "Dermal-Epidermal Separation. II. External Factors in Suction Blister Formation with Special Reference to the Effect of Temperature," *Ann Clin Res* 4(4): 236-246.

Azar et al. (2001). "Laser Subepithelial Keratomileusis: Electron Microscopy and Visual Outcomes of Flap Photorefractive Keratectomy," *Curr Opin Ophthalmol* 12(4):323-328.

Beerens et al. (1975). "Rapid Regeneration of the Dermal-Epidermal Junction After Partial Separation by Vacuum: An Electron Microscopic Study," *J Invest Dermatol* 65(6):513-521.

Willsteed et al. (1991). "An Ultrastructural Comparison of Dermo-Epidermal Separation Techniques," *J Cutan Pathol* 18(1):8-12.

van der Leun et al. (1974). "Repair of Dermal-Epidermal Adherence: A Rapid Process Observed in Experiments on Blistering with Interrupted Suction," *J Invest Dermatol* 63(5): 397-401.

Katz S I. (1984). "The Epidermal Basement Membrane: Structure, Ontogeny and Role in Disease," *Ciba Found Symp* 108:243-259.

Green et al. (1996). "Desmosomes and Hemidesmosomes: Structure and Function of Molecular Components," *FASEB J* 10(8):871-881.

SUMMARY OF THE INVENTION

Described here are methods and devices for producing a flap of epithelium on the eye. The methods are of a design that will produce the flap without also raising the underlying corneal tissue. The present invention includes mechanical non-cutting devices and methods to lift a generally continuous layer of epithelium from its supporting underlying corneal structure. The epithelial delaminator is used to create an epithelial flap that may be re-placed or positioned variously over an implant such as an ocular lens or over the site of a refractive surgical procedure such as LASEK.

The implants may be refractive lenses or diffractive devices or other devices (such as drug-delivery devices) and generally comprise one or more synthetic polymeric materials.

The epithelial delaminator may be mechanical in nature. Mechanical delaminators lift epithelium in a generally continuous layer from the anterior surface of the eye by application of a dissecting, non-cutting, mechanical force. Mechanical delaminators specifically include blunt dissectors and wire-based dissectors having wires that are passive or active as applied to the eye. The wires may rotate during the dissection or not, depending upon the variation described.

The application of heat to the epithelium, e.g., by exposure to heated water or a heated wire, or application of oscillatory or vibratory forces generally enhances the delamination process.

BRIEF DESCRIPTION OF THE DRAWINGS

FIG. 2C is a side, cross-sectional view of a variation of suction apparatus having a porous plate for supporting the epithelium.

FIG. 2D is a bottom view of the FIG. 2C device.

FIG. 2E is a side, cross-sectional view of a variation of suction apparatus having a foraminous insert used to support the epithelium.

FIG. 2F is a bottom view of the FIG. 2E device.

FIG. 3A is a side, cross-sectional view of a wire separating the epithelium from the corneal stroma.

FIG. 5A shows a partial cutaway of a jig used to limit or to control the path of the dissector on the cornea.

FIG. 5B shows a close-up of the FIG. 5A jig.

FIGS. 5D and 5E show two perspective views of the FIG. 5A jig.

FIG. 7B shows a side, cross-sectional view of an absorbent pad containing a chemical composition for lifting the epithelium on a portion of the corneal epithelium.

DETAILED DESCRIPTION

Figure 1A:
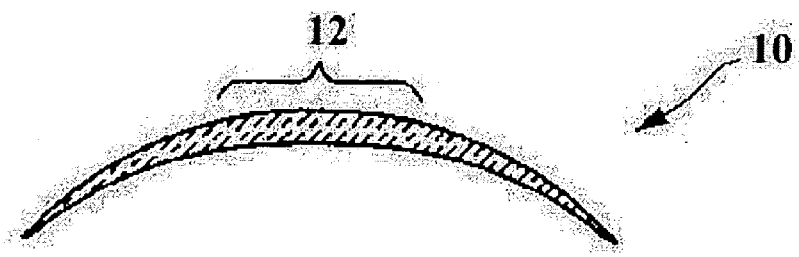
FIG. 1A is a side, cross-sectional view of a lens implant useful for correction of myopia.

As I noted above, described here are procedures for introducing subepithelial devices (e.g., ocular lenses) beneath the epithelium and typically on the anterior cornea surface, for lifting epithelium variously for placement of those subepithelial devices upon the cornea or for other surgical procedures, and for replacing epithelial tissue over the implanted subepithelial devices or surgical site. Devices for lifting epithelium from the surface of the cornea are described below as is the structure formed by certain of the subepithelial devices in contact with the replaced epithelium.

Procedures

Again, as I mentioned above, the term "epikeratophakia" refers generally to the implantation of donor corneal tissue (stroma) onto the surface of the eye where it ultimately resides between the native anterior corneal surface and the multilayered epithelium. Synthetic epikeratophakia, in turn, refers to the use of synthetic materials (instead of donor corneal stroma) for use in the exact same procedure. I have observed that the success of any epikeratophakia procedure is dependent on epithelial wound healing and epithelial coverage over non-epithelium covered surface (i.e. implant surface).

Epithelial wound healing over a non-epithelialized surface is dependent on the function of the epithelial cell. So-called "healing" epithelial cells are functionally and phenotypically different than epithelial cells in homeostasis (normally residing in an undamaged epithelium).

Epithelial cells in homeostasis, proliferate at the basal cell layer at a low rate and terminally differentiate as daughter cells are pushed towards the epithelial surface. At the basal cell layer, one major function of the epithelial cells is to provide adherence to the underlying stroma and another major function is the production of more epithelial cells. This is non-proteolytic, non-remodeling, and simply provides for a maintenance state.

Healing epithelial cells, on the other hand, are phenotypically and functionally different from homeostatic epithelial cells. Healing epithelial cells are undergoing migration and remodeling of the substrate onto which they are moving. Healing epithelial cells dissolve their intercellular attachments (desmosomes) and produce actin filaments for locomotive capability. In addition to migration, healing epithelial cells are resorbing/dissolving nonviable substratum from viable substratum. As such, these cells are producing proteases (e.g., interstitial collagenase, plasminogen activator, and matrix metalloproteinases).

In the classic epikeratophakia procedure, there is a direct stimulus that leads to transformation of the epithelial cell from quiescent homeostasis to metabolically active remodeling. That direct stimulus is the absence of epithelium over the epikeratophakic device. In the classic epikeratophakic procedure, there is a fundamental requirement that the device surface be resistant to proteolysis and be recognized as normal tissue. If the device surface does not have these properties, then the migrating epithelium may either destroy the surface or remain transformed to a resorptive remodeling machine. This is direct consequence of the absence of epithelium.

By use of my procedures of replacing epithelial tissue over an implanted subepithelial device or surgical site, the epithelium is kept in a state of homeostasis. The deleterious changes in epithelial cell function may be avoided.

A previously used surgical procedure intended to keep the epithelium in a homeostatic state is known as lamellar keratotomy and is performed using a stromal microkeratome. The prototype stromal microkeratome is the Barraquer microkeratome, a device developed by Dr. Jose Barraquer. The device includes an automated incision system that makes an incision in the body of the cornea with the incision plane oriented to produce a disc or flap of tissue comprising both corneal and epithelial tissue.

Microkeratome dissections are commonplace since the advent of LASIK. LASIK preserves the epithelium in homeostasis since it cuts through the cornea beneath the epithelium. The resultant surgical bed is reformed with laser ablation. Recently, hydrogel lenses have been produced that are specifically meant to reshape the surgical bed by an additive (non-ablative) means. In fact, laser refraction has been widely accepted by the public primarily because intact normal epithelium alleviates the sensation of pain in LASIK procedures.

A factor of my described procedure allows, as necessary, for the pristine preservation of the epithelium even when used in conjunction with such minimally disruptive implantation/surgery procedures as LASIK. However, my procedure avoids the portion of the now typical LASIK procedure, one that is an invasive, aggressive, and irreversible procedure that cuts into the stroma of the cornea, by lifting but the epithelium and preserving it in a homeostatic form. It is to be recalled that in a typical LASIK procedure, once an incision is made in the stroma of the cornea, that incision will either remain dehiscent or will overtly form an opaque fibrous scar. Either sequalae is irreversible. It is apparent that a "better" lamellar keratotomy would yield a "thinner" stromal flap or disc. My procedure produces what may be considered a pure epithelial flap where the plane of the "separation" is just beneath the inferior cell membrane of the basal epithelial cell and above the collagen I and collagen III of the anterior corneal stroma. I refer to the process of making a pure epithelial flap as epithelial delamination.

Creation of the surgical space for sub-epithelial device implantation is performed by epithelial delamination. Delamination of epithelium may be performed by the chemical, thermal, or mechanical devices and procedures discussed below. Common pathologic process that mimic epithelial delamination is blistering. Osmotic blistering (1M NaCl) achieves a separation at the basal lamina (lamina lucida) which results in a pure epithelial flap. Suction blistering also promotes a blister that results in a pure epithelial flap. Separation at the lamina lucida is also possible by applying a tensile force at the basal lamina. Since the lamina lucida is the "weakest link" of adherence, force along the basement membrane results in a blunt dissection along the lamina lucida. Forceful introduction of a mechanical probe or fluid can be used to achieve a blunt dissection to create an epithelial flap.

Once an epithelial flap is created, an "appropriate" sub-epithelial device may then be placed onto the delaminated corneal surface. Appropriate sub-epithelial devices may be chosen to provide relief from a variety of maladies: myopic refractive corrections, hyperopic refractive corrections, or even presbyoptic correction. Changes in the anterior surface curvature correct myopia by generally inducing a flatter corneal surface. Hyperopic corrections may be achieved by sub-epithelial devices providing a steeper corneal surface. Combinations of curvature changes may be used to treat presbyopia, for instance, a device providing a steep curvature change centrally and a flatter curvature at the perimeter of the device. Devices relying solely on curvature change to provide optical correction are typically, optically clear. Lenses relying on diffraction optics may have opaque or semi-opaque regions.

Diffraction-based, optical, sub-epithelial devices utilize diffraction patterns that create constructive interference. Multi-focal diffraction optical patterns may be used to treat presbyopic corrections or to correct existing simple refractive errors. Diffraction optical patterns may be introduced onto the surface of the delaminated cornea by printing them onto the subepithelial device. In overall effect, this would be similar to "tattooing" a pattern on the surface of the cornea.

Functionally, the subepithelial devices (both in structural design and materials) chosen for my procedures allow the substantially unperturbed flow of nutrients and metabolites from the anterior chamber of the eye, across the cornea to the living epithelium. This flow permits the long term continued functioning of the device. A discussion of appropriate materials is discussed below.

Because previous attempts to develop procedures involving synthetic epikeratophakic devices did not involve placement of epithelial tissue onto the surface of the device itself, the substrate chemistry of the device was of fundamental importance since it was to provide a proteolytically stable (non degradable) chemistry allowing both for adherence and, more importantly, migration of healing epithelial cells.

With my epithelial delamination and replacement procedure, it is not a clear requirement that the material surface chemistry promote an ideal cell-adhesive environment. In general, I believe that the that the chosen material simply be sufficiently biologically "inert" so as not to engender a foreign body reaction. The LASIK procedures have demonstrated clinically that a "free" lamellar corneal flap need not necessarily be affixed to the incised surgical bed for substantially effective vision correction. Indeed, successful revision of LASIK procedures rely on the surgeons' ability to lift the flap from the surgical bed. This tacit adhesion of the corneal flap to the surgical bed is sufficient to maintain effectiveness of the LASIK procedure.

In general, the described process involves the steps of separating the epithelium from the anterior surface of the corneal stroma desirably using one of the devices described below typically to produce a substantially continuous sheet and with a flap (or perhaps, pocket) shape or hinging attachment to the eye, applying a subepithelial lens or other implant device to the site, and re-applying at least a portion of the epithelium to the exterior surface of the implant. Although many of the physiological benefits occurring as a result of the placement of healthy epithelial flap will inure with use of replaced epithelium that is not attached via a flap or hinge to the eye, the benefits are greater and the procedure itself is much more easily practiced by surgeons (experienced and novice) and by non-surgeons if the epithelium is maintained as a flap or pocket.

Subepithelial Devices

Suitable subepithelial devices for the described procedure include devices or implants that correct or improve visual acuity or simply change the user's vision in some way, perhaps by changing the eye's natural range of focal lengths to create a telescopic or microscopic effect. Suitable devices or implants may also be used for other medical or cosmetic reasons, e.g., for reasons as diverse as drug delivery or as bandages or to change eye color. The ocular corrective implants, of course, may be refractive or diffractive in principle of operation.

Because the epithelial layer itself has little refractive power, suitable ocular corrective implants may have a physical shape generally of a size and configuration similar to soft contact lenses. These implants, upon placement on the cornea and beneath the replaced epithelial flap, supplements the curvature of the cornea to correct abnormal conditions such as astigmatism, myopia, hyperopia, presbyopia, and aphakia.

The overall diameter of these ocular implants lens is functionally appropriate to perform the desired correction, and generally is less than about 25 mm and may be between 10 and 15 mm., or even smaller such as 5 to 10 mm. The thickness of the lens is, again, functionally appropriate to perform the desired correction. The ocular implants generally will have a thickness less than 300 μm, often between 5 and 200 μm, and often between 5 and 100 μm.

Figure 1B:
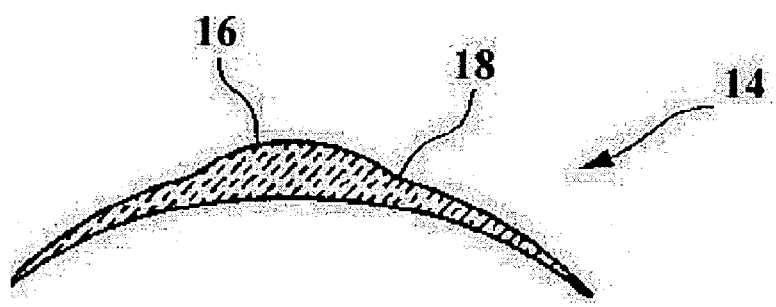
FIG. 1B is a side, cross-sectional view of a lens implant useful for correction of aphakia.

FIG. 1A shows a lens implant (10) suitable for myopic patients having a generally circular region (12) in the center that is flattened in its anterior curvature. In correction of aphakia, a suitable lens (14) such as is shown in FIG. 1B may be used. Such lens has a comparatively thicker center (16) and a thinner perimeter (18). Again, in general the shapes discussed here are similar to those found in the so-called "soft" contact lenses and instruction may be had from that technology relating to the overall form of the lenses selected for correcting specific ocular maladies.

Figure 1C:
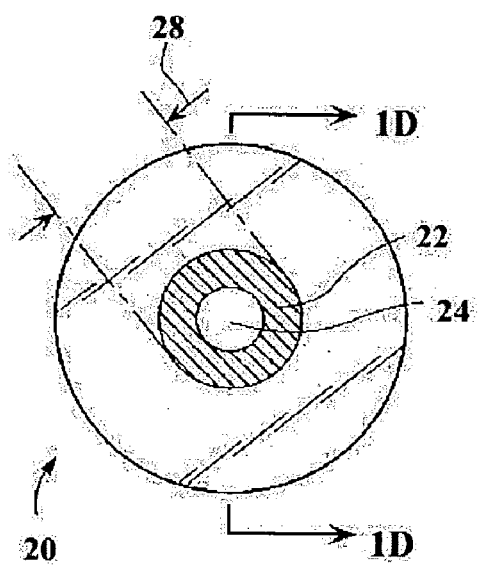
FIG. 1C is a front view of a lens implant useful for correction of presbyopia.
Figure 1D:
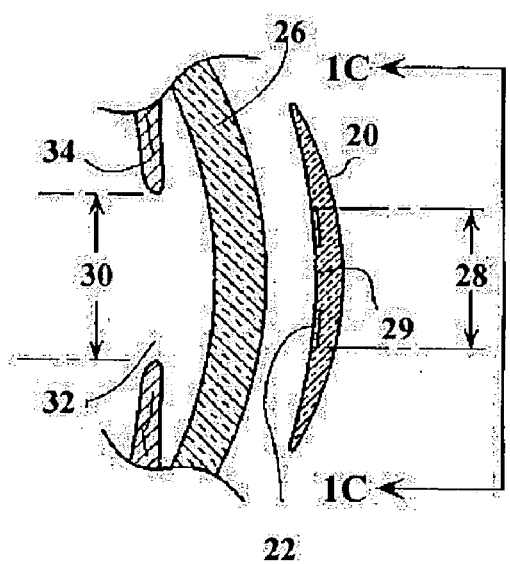
FIG. 1D is a side, cross-sectional view of a lens implant useful for correction of presbyopia.

FIGS. 1C and 1D show a lens that may also be used to correct presbyopia. In particular, to treat presbyopia, the lens (20) is also provided with an generally opaque annular region (22) adjacent the center of the device. The open center (24) preferably has piano-lens characteristics and an effective diameter of less than about 1.5 mm, preferably between about 0.5-1.5 mm, and most preferably between 0.75 mm and 1.75 mm. The diameter of that open center (24) or central area or "pinhole" is generally formed and selected to be less than the pupillary diameter of the host eye in daylight. This creates a refractive "pinhole" effect, thereby lengthening the overall effective focal length of the eye and minimizing the need for the eye to accommodate. Bifocal lens designs can also be incorporated, e.g., concentric rings, segmented or sectors of the annular region or ring, or progressive diffractive.

FIG. 1D shows a side, cross-sectional view of lens (20) as found in FIG. 1C, adjacent the anterior surface of a cornea (26) to illustrate certain features of this variation. The outer diameter (28) of the opaque annular ring (22) is generally selected so that it is smaller than the diameter (30) of the pupil (32) in the iris (34) in low light conditions. In this way, the eye's cornea and lens and the inventive lens cooperate in such a way that incident light passes both though the center of the opaque ring (24), but more importantly, around the periphery of the opaque ring (22), to allow corrected sight during low light conditions.

The annular ring (22) may be situated on the lens implant in various ways, for insistence, by placement of a suitable dye, i.e., by "tattooing", or by placement of a substantially opaque biocompatible member of, e.g., Dacron mesh or the like, on the posterior surface to filter light rays. Extrusion, assembly of lens from various components, painting, dying, or any other method of placing the desired pattern would be suitable based upon this description. Another placement of the annular ring (22) includes placement on the anterior surface of the lens. The annular ring (22) itself preferably is quite opaque, e.g., passing less than about 80% of incident visible light, but may be chosen in such a way to be less opaque or to correct other maladies such as colorblindness by shifting an incident color into a visible range by color refraction or the like.

Figure 1F:
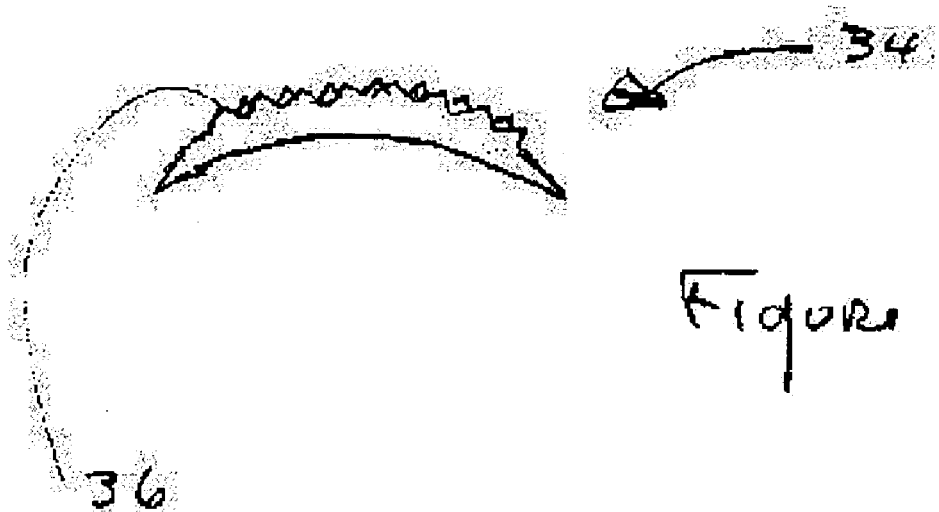
FIG. 1F is a side, cross-sectional view of a lens implant having a Fresnel-type lens portion.
Figure 1E:
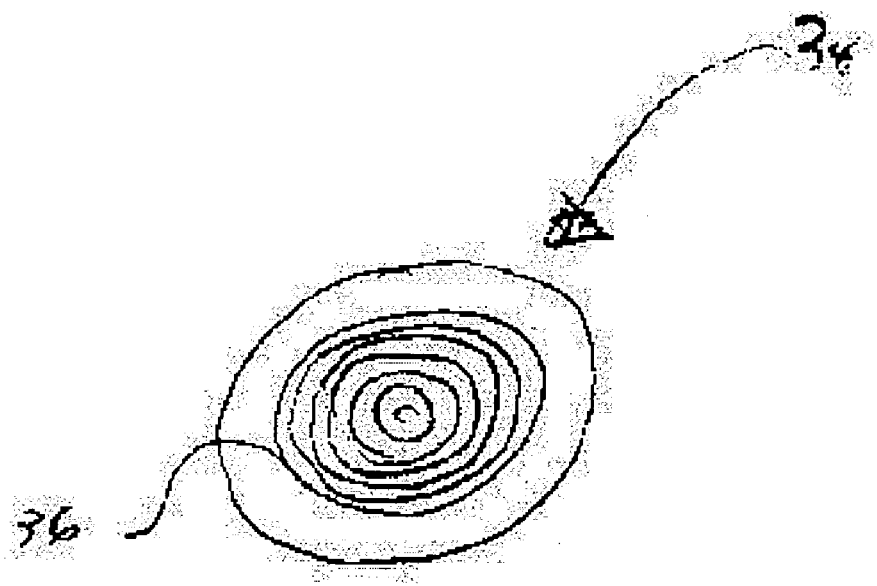
FIG. 1E is a front view of a lens implant having a Fresnel-type lens portiona.

Other refractive implant designs are also suitable. FIGS. 1E and 1F show, respectively, a front view and a side, cross sectional view of a Fresnel-like lens implant (34) that may be used as an implant beneath the replaced epithelium. Circular rings (36) having a triangular cross section cooperatively refract incident light to form the resulting image. Although the rings (36) are shown without a covering, the placement of a covering having an appropriate index of refraction to present a smooth surface to the epithelium is within the scope of this description.

Although most refractive designs are generally circular in shape, my procedure may be used with other shapes such as the generally rectangular corneal onlay described in U.S. Pat. No. 6,228,113.

Diffractive designs for the implant are also suitable. For instance, diffractive lens designs comprising lens elements with light-affecting surfaces made using known techniques for producing diffractive surfaces are suitable. Typically, the lens elements, perhaps grooves in a polymeric surface or collections of filamentary elements appropriately arranged, have light-affecting surfaces with differential adjacent surface dimensions nearing the wavelength of visible light.

Subepithelial Implant Material Compositions

Materials that are appropriate for these subepithelial devices vary widely. The devices or implants may comprise, consist essentially of, or consist of any of the materials specified below and elsewhere herein.

Various classes of materials are suitable. For instance, hydrophilic polymers, hydrophobic polymers, polymers that form hydrogels, biopolymers, porous polymers, and porous ceramics and glasses. Generally, polymeric compositions suitably used as contact lenses are suitable for my described method. Conventional soft lenses typically are primarily hydrogels derived from a variety of hydrophilic monomers or polymers that have either been crosslinked or insolubilized in water by some other mechanism, such as by introduction of crystallinity or by varying relative hydrophobic/hydrophilic properties. The polymers normally contain upwards of 45% water with a Dk value of 8-25 ($\times 10^{-11}$ cm$^2$/sec) (ml O$_2$/ml mmHg) at 35° C. Another soft lens composition class contains hydrophobic polymer systems, e.g., silicone elastomers, above their glass transition temperatures ($T_g$).

I prefer hydrogel-forming polymer compositions because of their ready ability to transport or carry large amounts of fluids and nutrients, etc. across the lens thickness to the epithelial layer. Physical polymer blends or alloys, composite polymer constructs, coated or treated polymers tending to enhance epithelial cell growth, and the like are suitable.

Hydrogel compositions typically comprise hydrophilic polymers, perhaps containing an amount of hydrophobic polymers that, when synthesized, tend to absorb water rather than dissolving. Hydrophilic polymers may, for insistence, be synthesized from monomers or macromers such as: monomers of hydroxy-substituted $C_1$-$C_4$-alkyl acrylates and methacrylates, including hydroxyethyl methacrylate (HEMA), hydroxyethylacrylate or hydroxypropylacrylate, acrylamide, methacrylamide, N-mono- and N,N-di-$C_1$-$C_4$-alkyl acrylamides and methacrylamides which may be hydroxy-substituted in the alkyl moiety, hydroxy-substituted $C_1$-$C_4$-alkylvinylethers, allyl alcohol, vinyl acetate, vinylically unsaturated carboxylic acids having a total of 3 to 5 carbon atoms, for example acrylic or methacrylic acid, N-vinylpyrrolidone and N-acryloylmorpholine; hydrophilic macromers include vinylfunctionalized polyvinyl alcohol, polyalkylene oxide (e.g., polyethylene oxide) or N-vinylpyrrolidone homo- or copolymer perhaps with one or more ethylenically unsaturated double bonds. Included in the suitable hydrogel-forming polymer class are the venerable polymers or copolymers of HEMA and N-vinyl-pyrrolidone, or copolymers of these polymers or their copolymers with methylmethacrylate or acrylic acid, as may be prepared by the catalytic polymerization of those monomers under heating in the presence of a suitable catalyst. See U.S. Pat. Nos. 4,693,715; 5,300,116; and 5,458,819.

U.S. Pat. No. 5,786,434 discloses a suitable hydrogel, water-absorptive soft contact lens material made up of copolymer prepared by polymerizing a monomer mixture of 15 to 40% by weight of N,N-dialkylmethacrylamide or N,N-dialkylacrylamide, 10 to 30% by weight of N-vinyllactam, and 30 to 70% by weight of bis(silicon-containing alkyl) fumarate.

Porogens such as optionally substituted poly(alkylene)glycols (e.g., those having up to 7 carbon atoms in each alkylene unit, particularly polyethylenglycols or polypropyleneglycols) may be added during polymerization to provide pores, if so desired, in the final polymer.

Many such polymers have been modified to promote cell growth by, for instance, copolymerizing the underlying hydrophilic monomer (using crosslinkers) with a monomer containing a sulfo group such as ethylenically unsaturated 2 to 18 C compounds having a sulfo group or a suitable salt thereof, such as methallylsulfonic acid, styrenesulfonic acid, sulfopropylmethacrylate, sulfopropyl-acrylate, 2-acrylamido-2-methylpropanesulfonic acid, vinyl sulfonic acid, or their salts such as sodium methallylsulfonate, sodium styrenesulfonate, potassium sulfopropylmethacrylate or potassium sulfopropylacrylate.

Other polymeric systems that support cell growth include polyperfluoropolyethers as shown in U.S. Pat. Nos. 4,440,918, 4,818,801, and 5,994,133 and polyperfluoroalkylpolyethers as shown in U.S. Pat. No. 6,225,367. These polymers and the others mentioned herein may be physically or chemically made into porous materials if the specific utility makes it desirable.

Hydrogels comprising natural polymers and hydrophobic monomers are acceptable. One such polymer is shown in U.S. Pat. No. 5,632,773 and is a composition of collagen covalently bonded to a hydrophobic polymer, the monomers of which have a fractional polarity less than that of methyl methacrylate.

Biopolymers such as collagen I, collagen III, collagen IV, gelatin, crosslinked heparin, crosslinked hyalouronic acid, chondroitan sulfate, fibronectin, laminin, and the like may be used.

Other non-hydrogel polymers such as polyethylene, polypropylene, polyurethanes, etc. are suitable, particularly when treated to enhance cell growth or to allow liquid transport. U.S. Pat. No. 4,607,617 teaches the use of polysulfones in contact lenses. For instance, U.S. Pat. No. 6,176,580 shows the use of silicone elastomers, silicone-containing macromers including those disclosed in U.S. Pat. Nos. 5,371,147; 5,314,960, and 5,057,578, hydrogels, silicone-containing hydrogels, and the like and combinations thereof. The surface contained a siloxane or a siloxane functionality such as polydimethyl siloxane macromers, methacryloxypropyl polyalkyl siloxanes, and mixtures thereof, silicone hydrogel or a hydrogel, such as etafilcon A.

Microporous non-hydrogels as shown in U.S. Pat. No. 5,713,957 comprise polymers and copolymers of acrylics, polyolefins, fluoropolymers, silicones, styrenics, vinyls, polyesters, polyurethanes, polycarbonates, cellulosics or proteins such as collagen based materials are suitable.

Epithelial Lifting Devices

For any integument surface such as the skin, respiratory epithelium, gut epithelium, and cornea, there is an epithelial cell layer that is adherent to an underlying basement membrane. When epithelium is separated from its basement membrane and underlying collagenous tissue, a subepithelial blister is formed. In general, gross separation less than 1 mm in diameter is known as vesiculation and separation greater than 1 millimeter in diameter, a true blister.

A continuous layer of corneal epithelium may be separated from or lifted from the anterior surface of the eye by applying various mechanical forces to this anterior surface, or to the basal cell layer, or to the junction between the basal cell layer and the Bowman membrane (the "lamina lucida"). The term "continuous" as used herein means "uninterrupted". The term "mechanical force" as used herein refers to any physical force produced by a person, instrument, or device. Examples of mechanical forces include suction, shearing, and blunt forces.

Mechanical forces are applied to epithelium such as corneal epithelium by epithelial delaminators. As used herein, the term "epithelial delaminator" refers to any instrument or device that separates epithelium from the basement membrane by application of a mechanical force. Epithelium may also be separated from or lifted from the anterior surface of the eye by contacting the surface with a chemical composition that induces separation of the epithelium from the underlying stroma.

Mechanical Epithelial Delaminators

Figure 2A:
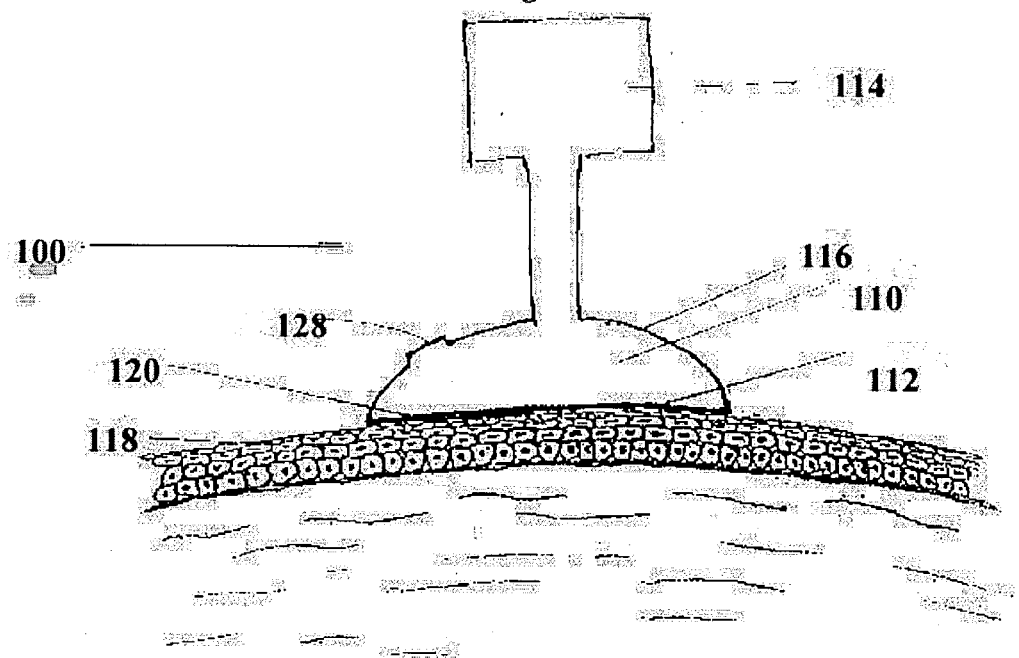
FIG. 2A is a side, cross-sectional view of a suction apparatus on the corneal epithelium.

In a first variation of the mechanical epithelial delaminator, the delaminator is a suction apparatus as shown in FIG. 2A. The suction apparatus (100) includes a suction chamber (110) that has an epithelial contact surface (112) and a vacuum source (114). The suction chamber (110) and vacuum source (114) are in vacuum communication and may be connected by such attachments as luer connectors or flexible tubing.

Figure 2B:
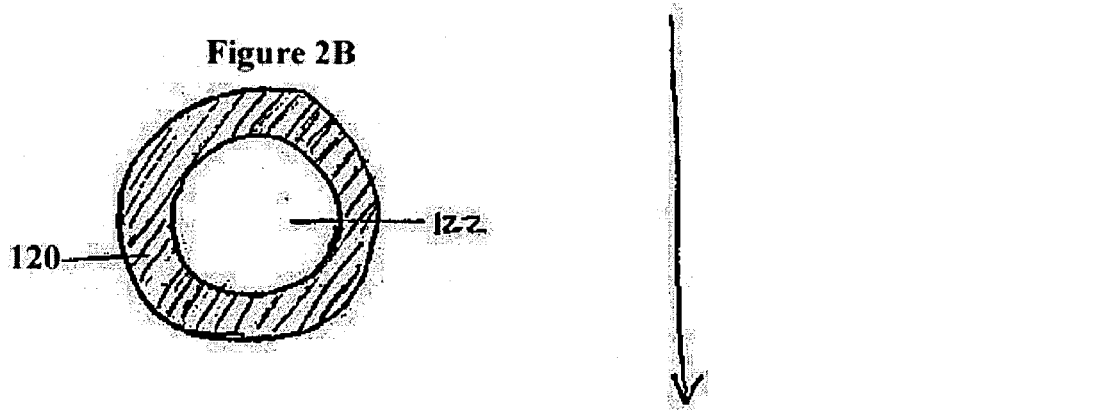
FIG. 2B is a bottom view of the suction apparatus ring used to contact the corneal epithelium.

The suction chamber (110) may be provided in any shape, but in general is a hemispherical cup or cup conforming to the anterior surface of the eye. The wall of the suction chamber (116) may be made of a deformable material and transparent so that the epithelium (118) is visible upon placement of the suction apparatus on the anterior surface of the eye. The suction apparatus may also have an epithelial contact surface (120) that is preferably ring shaped, but any desired shape may be used, but in any event, is shaped functionally to provide an appropriate vacuum seal with the surface of the epithelium. FIG. 2B shows an inferior view of the epithelial contact surface (120) of FIG. 2A. The ring (120) may be made of materials such as metals, polymers, and elastomers, or mixtures thereof.

The vacuum source (114) of suction apparatus (100) is typically a manual pump or a motorized pump, but may also be a syringe. The amount of negative pressure created by the pumps may be monitored with a pressure gauge. When using a syringe, suction is adjusted by movement of a retractable piston.

In use, suction apparatus (100) is placed on the anterior surface of the eye to contact the epithelium (118). A vacuum is created by the vacuum source (114) and the applied negative pressure to area (122) circumscribed by epithelial contact surface (120), is in an amount sufficient to lift the epithelium in a continuous layer. If desired, applying an intermittent or continuous, translational, oscillatory, or torsional force may also enhance epithelial separation.

FIGS. 2C-2E show other variations of the suction device specifically using supports within the vacuum space of the device. In FIGS. 2C and 2D, the suction device (140) includes a porous or perforated plate (142) having small incorporated passageways (144). The epithelial flap is drawn against the bottomside of the plate (142) upon introduction of suction.

Similarly, suction device variation (150) includes a foraminous insert (152) having a lower surface (154) that may be formed to accept an epithelial layer desirably without substantial deformation. The epithelial flap may be loosened upon release of the vacuum. Suitable foraminous inserts are varied in composition. The insert may be, for instance, porous sintered metal or polymer. Similarly, the insert may be a reticulated foam or other polymeric insert made to pass vacuum from the vacuum port (156) to the support surface.

Figure 2G:
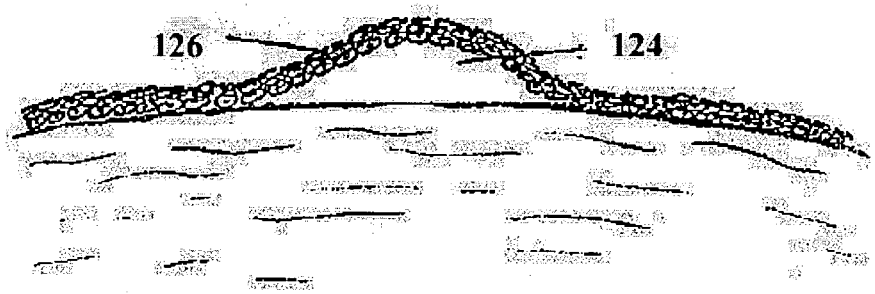
FIG. 2G is a side, cross-sectional view of a suction blister formed by the suction apparatus of FIG. 2A.

FIG. 2G shows a subepithelial blister (124) formed by raised epithelium. The separated epithelium (126) may then be manipulated to create an epithelial flap.

Pathophysiologically, epithelium (118) is lifted when hemidesmosomes lose their adherence to the basement membrane. However, unlike LASEK, where epithelial cells are killed, suction blistering results in an epithelium that is intact as a substantially continuous layer and viable, i.e., able to immediately restore normal epithelial functions.

Prior to this invention, suction blistering was only known as a method of epithelial delamination in skin. Suction blisters in skin were originally used as a laboratory tool to determine the pathophysiology of the autoimmune skin blistering diseases.

Mechanical epithelial delaminators may also be blunt dissectors. Blunt dissectors have non-cutting surfaces that are appropriate for placement between the epithelium and the collagenous stromal tissue. As used herein, the term "noncutting" means that the blunt dissector does not have the ability to incise into the stroma of the cornea when used with normal force. I believe that my blunt dissectors separate the epithelium from the stromal layers of the cornea in the basal membrane zone at the natural point of weakest attachment, i.e., the lamina lucida. The so-separated epithelium does not contain substantial amounts of corneal stromal tissue, or for purposes of this invention, does not contain any more than an insubstantial amount of the stromal tissue when the procedure is practiced on "normal" eyes (those having no artifacts due to injury or to disease). The so-separated epithelium does not contain Collagen Type I or Type III as may be found in the stromal tissues.

Figure 3B:
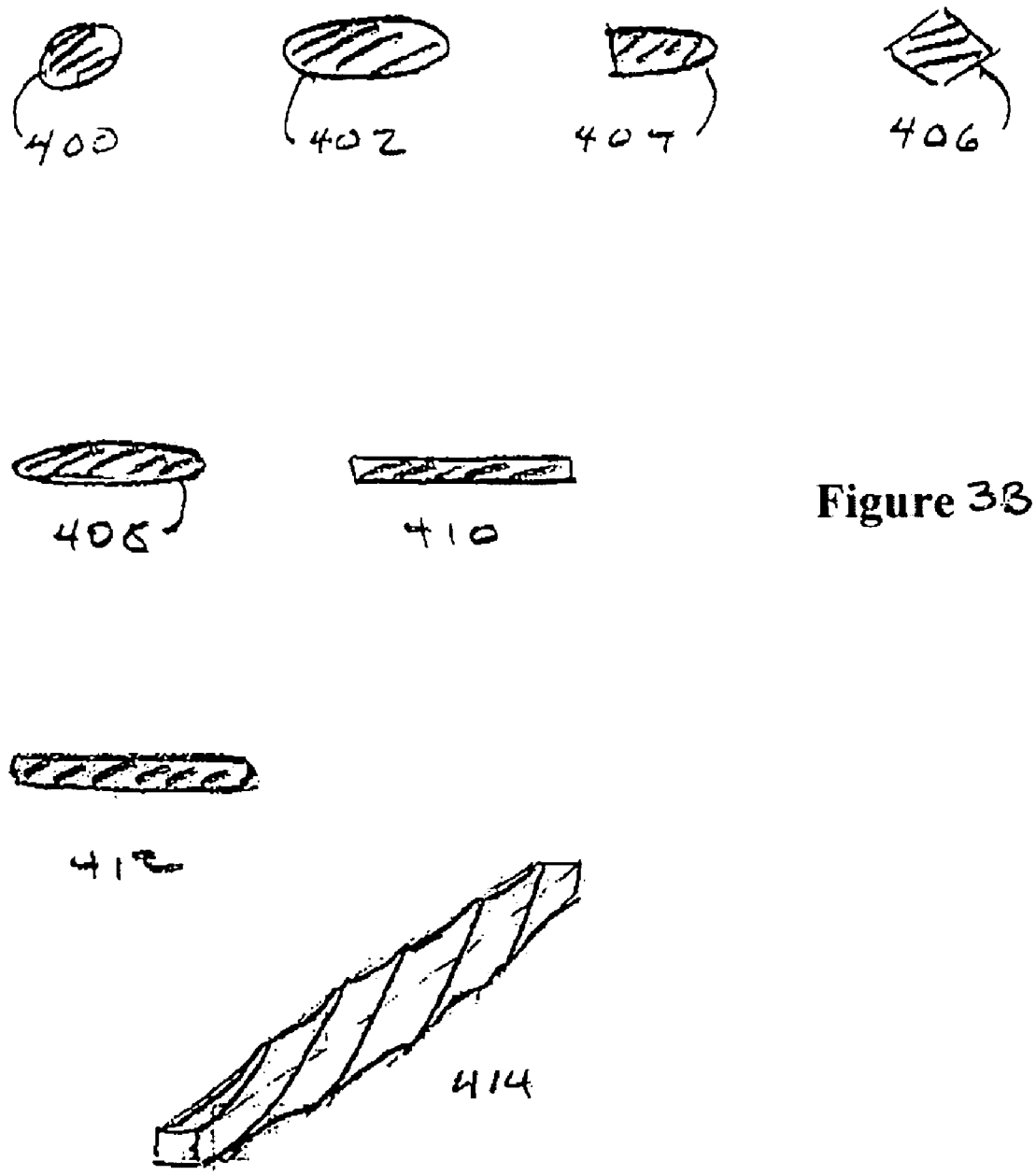
FIG. 3B shows a number of wire cross-sections and configurations.

In one variation, the blunt dissector is a small gauge wire that is inserted under the epithelium and moved parallel to the surface of the cornea to separate the epithelium from the stromal tissue. FIG. 3A shows a side, cross-sectional view of a wire (200) that is inserted between the epithelium (202) and stroma (204) to create an area of separation (206). The wire may be continuously or intermittently rotated, either by "rolling" the wire or by rotating it about an axis normal to the front of the eye, e.g., like a vane of a ceiling fan rotating about an axis parallel to the floor, or vibrated during dissection of the epithelium (202). The separated epithelium (208) may then be reflected back or peeled to expose the underlying stromal tissue (204).

I have found that of a wire having an effective diameter similar in size to the thickness of the basal cell layer, e.g., about ½ mil to 3.5 mils. (0.0005 to 0.0035"), but often about 1.0 mil to 3.0 mils (0.001 to 0.003"), and by experience, a round wire having a diameter near 2.0 mils is excellent. Furthermore, by proper selection of the stiffness of the wire (by adjustment of tension in the installed wire and/or selection of inherent stiffness of the material in the wire), the wire will dissect the junction between the epithelium and the stromal layers rather than cutting either the epithelium or the Bowman's membrane. An appropriate range of wire tension is 15 kpsi to 35 kpsi, perhaps 25 kpsi to 32.5 kpsi, often 25 kpsi to 30 kpsi. From a functional point of view, I refer to this ability to separate the epithelium from the underlying stroma without cutting the fibrils of that underlying stroma as "non-cutting."

Referring to FIG. 3A, I have depicted the wire dissector (200) as slightly depressing the stromal surface (204). Although I believe this to be an accurate depiction of the way in which my procedure and device works, I do not wish to be bound by that theory. Nevertheless, some depression of the stroma beneath the epithelium may be observed during use of the wire dissector described here. The dissector wire, when passed across an eye beneath the epithelium at a direction generally perpendicular to the wire itself, appears to pull the stroma below and away from the epithelium at the leading edge of the wire dissector.

Based on this information, the cross sectional shape of the wire need not be round to achieve the noted functional dissection, but may be of any suitable cross-section that bluntly dissects the corneal tissues to separate the epithelium from the stromal surface without removing stromal tissue. By "wire" and by the term "wire structures" I mean structures including variously: a) single strands of elongated materials having, for instance, the cross-sectional shapes discussed just below and b) structures including two or more strands variously not wound together, wound together, and braided together. Examples of single strand cross-sectional shapes are found in FIG. 3B: round (400), oval (402), truncated oval (404), square (406), ellipsoid (408), rectangular (410), rectangular with a bull nosed leading edge (412), and others. Again, the shapes are teamed with a material of construction and a tension to achieve the "non-cutting" dissection function discussed elsewhere. Relatively smooth surfaces are desirable for this service and allow ease of movement between the stroma and the epithelium.

Furthermore, the wire itself need not necessarily have a constant cross-section nor be uniform across its length just so long as it is able to perform the "non-cutting" dissection function. For instance, the scope of this invention includes twisted or helical wires (414), such as the variation shown in FIG. 3B, with a square cross-section. A twisted wire may be used with other cross-sectional variations such as the oval, ellipsis, rectangle, and other non-circular forms. The oval and elliptical shapes, when twisted, are quite gentle to the eye and may be positioned in such a way that the lifting force on the epithelium is high at the center of the epithelium and yet lower at positions adjacent that center.

Figure 3C:
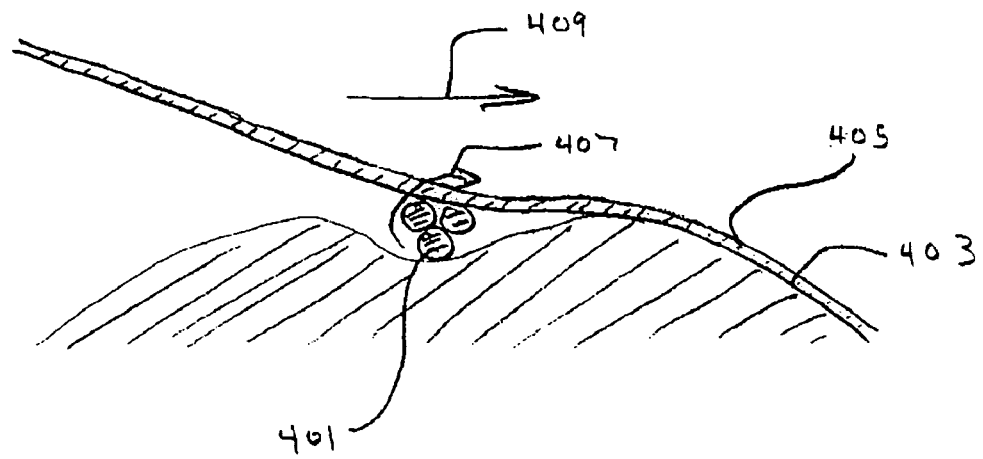
FIGS. 3C and 3D show rotation of the wire structure to separate the epithelium.
Figure 3D:
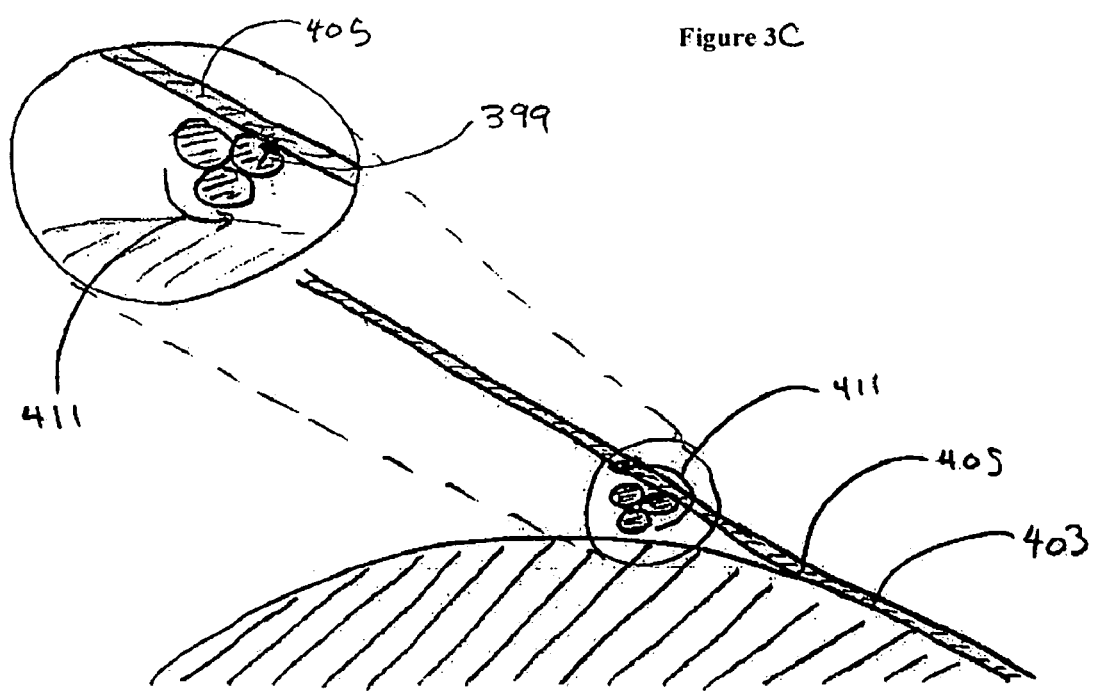
Figure 3E:
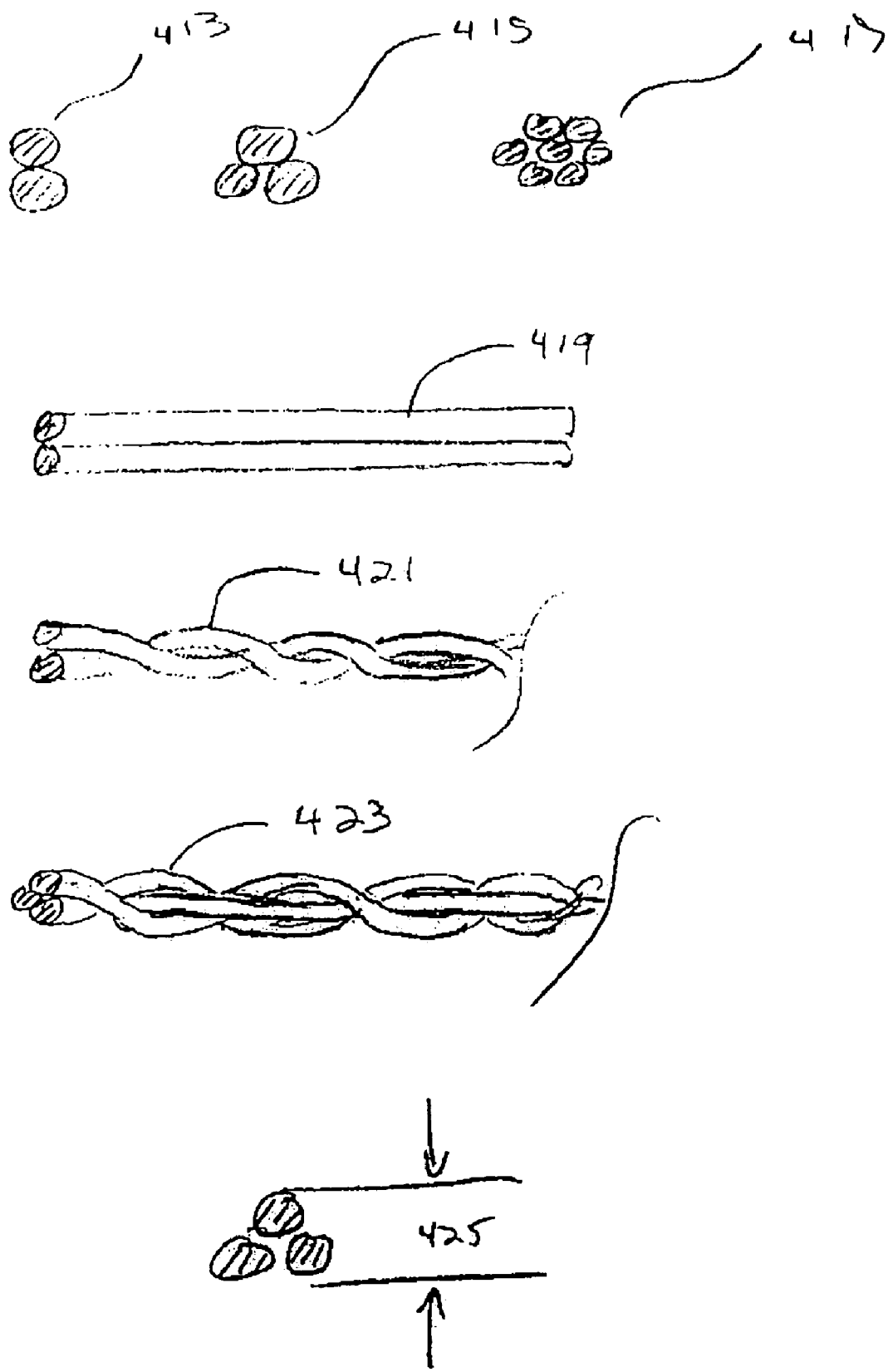
FIG. 3E shows various configurations of the multi-wire wire structure.

Other variations of the wire-based dissector that I believe to be quite gentle to the eye are shown in FIGS. 3C, 3D, and 3E. These wire structures are made up of multiple filaments of wire, filaments such as those having the cross-sectional structures shown in FIG. 3B.

As shown in FIG. 3C, the wire structure (201) is passively rolled across the corneal surface (403) below the epithelium (405) engendering a measure of "traction" on the corneal surface (403) but not causing a sliding friction on that surface. As shown there, the wire structure (201) rolls across the corneal surface (403) in a clock-wise direction (407) as the delaminator passes in a left-to-right direction (409). On the other hand, as shown in FIG. 3D, the epithelium (405) may be grasped and held in tension and the wire structure (401) lifted away from, perhaps even separated from, the corneal surface (403) to allow the wire structure (401) to separate the epithelium from the cornea. This variation appears to have a benefit in enhancement of the ease of separation of the epithelium from the corneal surface. The rotation of the wire structure is envisioned to engender a series of forces each nearly perpendicular to the underside of the epithelium and each force occurring as a new wire rotates into contact with the epithelium. Note the force arrow (399) shown in the inset of FIG. 3D.

A second variation is that the rolling motion of the wire structure or wire may be powered. A third variation is that the multi-wire structures, as noted elsewhere with respect to the twisted wires shown in FIG. 3B, need not necessarily be rotated at all.

FIG. 3E shows various configurations of the wire structure, e.g. with two wires (413), three wires (415), and multiple wires (417). Any reasonable number of wires (e.g., 3, 4, 5, 6, 7, 8, etc.) in the structure that will meet the separation function will be suitable. The wires may be laid side by side (419). They may be simply twisted (421) or they may be braided (423) to form a determinate structure. The desired diameter (425) may be the "effective" diameter discussed above. Again, these desirably are allowed to roll as they are moved over the eye to provide separation of the epithelium.

Figure 3F:
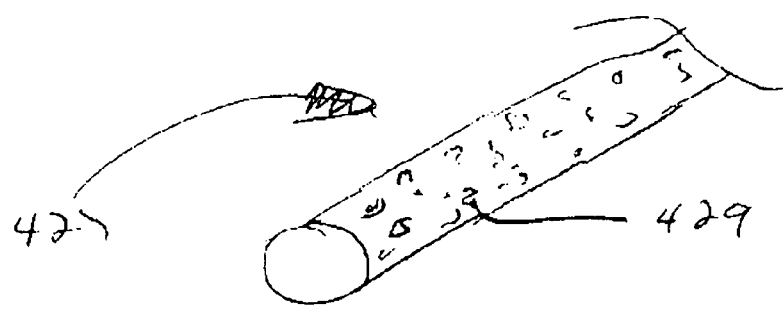
FIG. 3F shows a wire structure having a roughened surface used primarily in the rotating wire dissector assembly.

Finally, a roughened wire (427) is found in FIG. 3F. This surface may be attained by etching, sandblasting, etc. This lack of smoothness allows the wire (427) to roll about the eye with better control of the device and better separation of the epithelium. Surface roughening may be applied to the multiple wire structures as well.

Figure 3G:
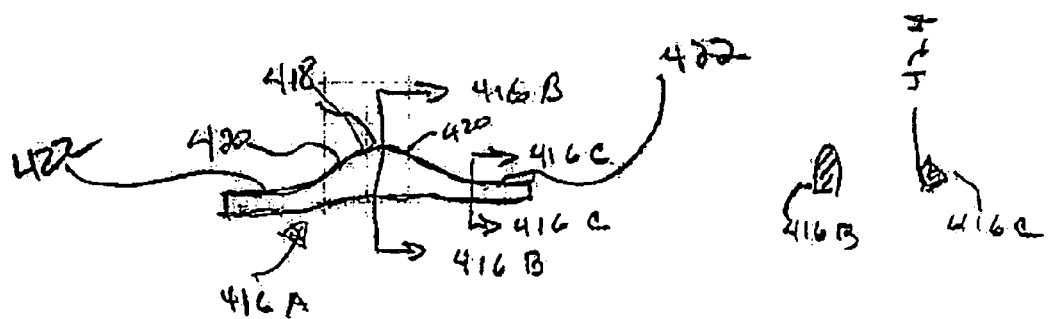
FIG. 3G shows a non-helically twisted delaminator wire.

In FIG. 3G, another variation of twisted wire having a non-uniform cross-section and a non-helical twist is shown. In FIG. 3G, I show a top view of a wire (416A) having a prow (418), of a type, or leading edge (416B) that, when pulled or pushed at the lamina lucida, functions as a blunt dissector that has adjacent shoulders (420) that move in a skewed fashion in that adjacent tissue area. In this variation, the narrowed shaft sections (422) are twisted in a single direction (see 416C) to provide increased distance from the lamina lucida to the upper surface (424) of the wire (418C). When moved along the lamina lucida, the variation provides a slight rolling motion to the epithelial layer, analogous in shape to the way a child rolls his tongue.

The materials making up the wire are not critical to the dissector structure, except to the extent that they are able to perform the noted function. The materials of construction may be metallic, e.g., steels, stainless steels, superelastic alloys including nitinol (Ni/Ti) or polymeric, e.g., Nylons, polyaramids, polyethyleneterephthalate and other polymers making strong fibers or mixtures, e.g., coated metals wires with PTFE coatings.

Figure 4A:
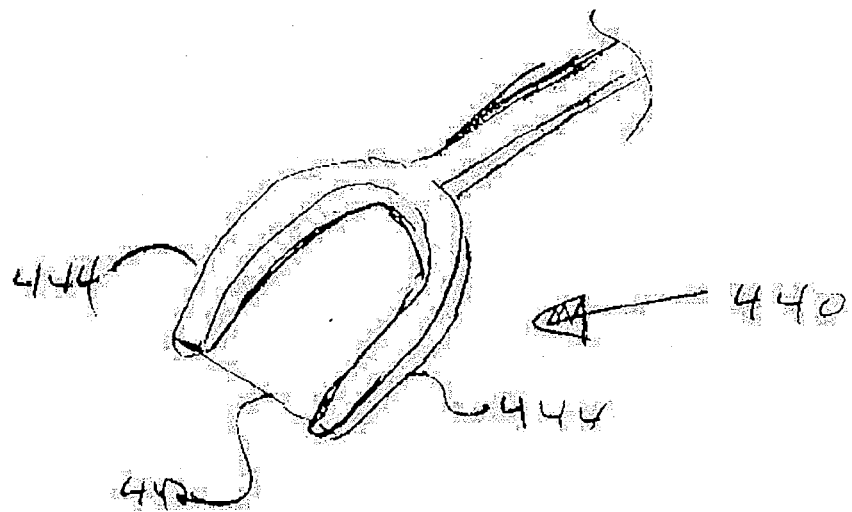
FIG. 4A shows two yoke configurations for the dissector.

Most of the variations discussed just above may be mounted in such a way that the wire is suspended between two sites, perhaps longitudinally pre-tensioned, perhaps allowing generally longitudinal tension to develop as the wire is pulled along the lamina lucida. Examples of suitable wire suspenders or "yokes" are shown in FIG. 4A. A first example of the yoke (440) suspends the dissection wire (442) between two yoke arms (444) having a fairly flat configuration so that the eye surgeon manipulating the device is able easily to see the dissection taking place below the epithelium and easily to position the tool for inception of the delaminating procedure. Similarly, yoke (446) has arm (448) that provides the surgeon with vision of the procedure and room beneath the shaft (450), typically having a handle, for additional room for grasping, etc.

Figure 4B:
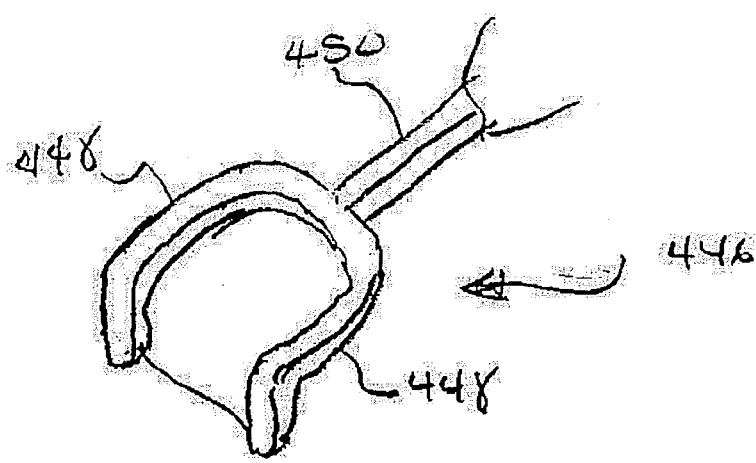
FIG. 4B shows a pathway for applying the dissector to a cornea.
Figure 4B:
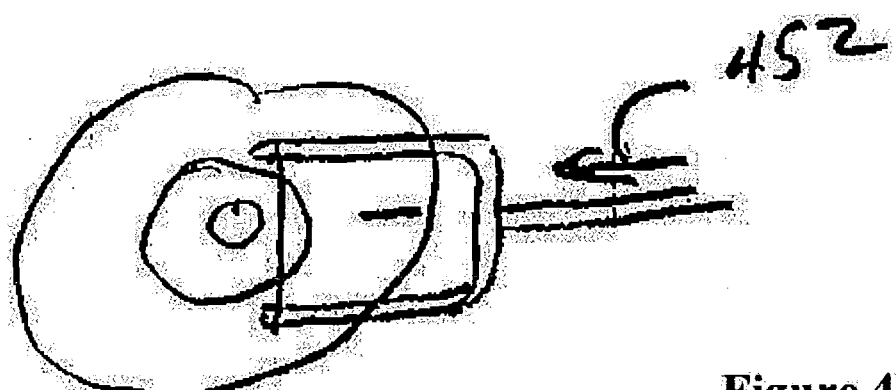
Figure 4C:
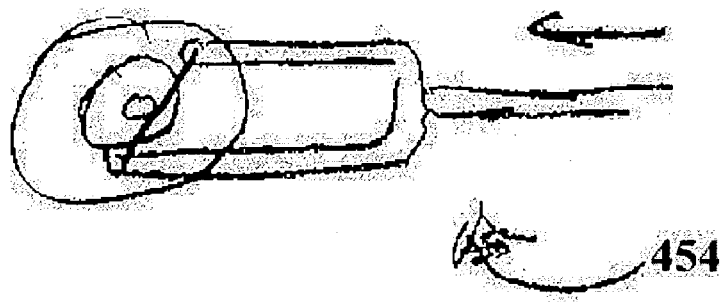
FIG. 4C shows a skewed yoke configuration for the dissector.

The variation shown in FIG. 4A are generally to be used by passing the wire in a motion in line with the axis of the handle (see FIG. 4B)—note direction arrow (452). This has proven to be quite effective in easily removing epithelium without harm. However, as shown in FIG. 4C, the wire may be moved obliquely through the lamina lucida using a yoke (454) constructed for that purpose. Note the direction of motion (456) shown in that FIG. 4C.

Figure 4D:
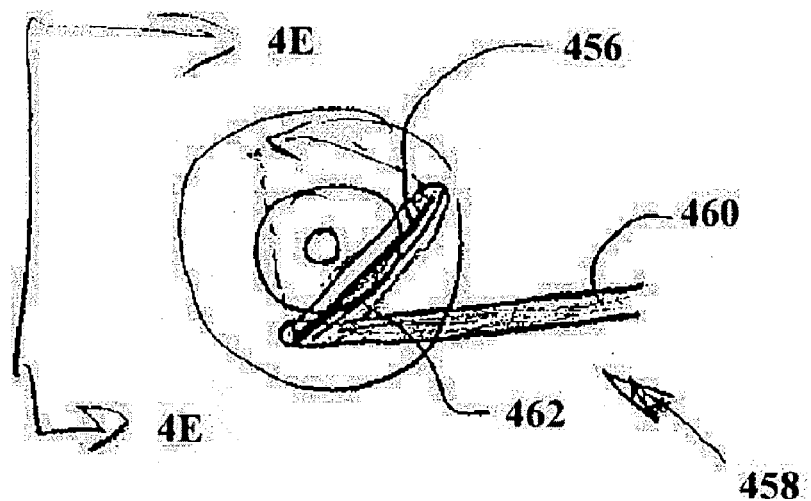
FIG. 4D shows a rotating yoke configuration for the dissector.
Figure 4E:
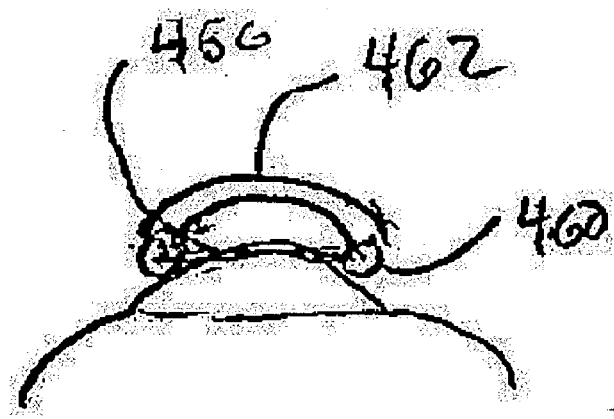
FIG. 4E shows a side view of the FIG. 4D skewed yoke configuration.

Further, the wire (456) may be rotated as shown in FIGS. 4D and 4E. In this variation, the two arms of the yoke (458) are not fixed with respect to each other. One arm (460) is fixed with respect to a rotating arm (462). The wire (456) rotates with the rotating arm in a partial arc that, at least partially, dissects the epithelium from the stroma.

As will be discussed below, dissection using wire may be used with forms or "jigs" to limit the dissection of the epithelial membrane to a flap. Wire dissectors, as described here, may also be oscillated or vibrated to enhance the dissection step.

First, repetitive motion of the wire dissector may help with the rate and ease of the dissection step. The wire may be oscillated or vibrated in a variety of ways, e.g., the wire may be simply vibrated in a plane generally having the movement or structure generally in the direction of the intended movement of the wire during the dissection step. In the variation shown in FIGS. 4A, 4B, and 4C, that stroke would be along the longitudinal axis of the handle.

Figure 4F:
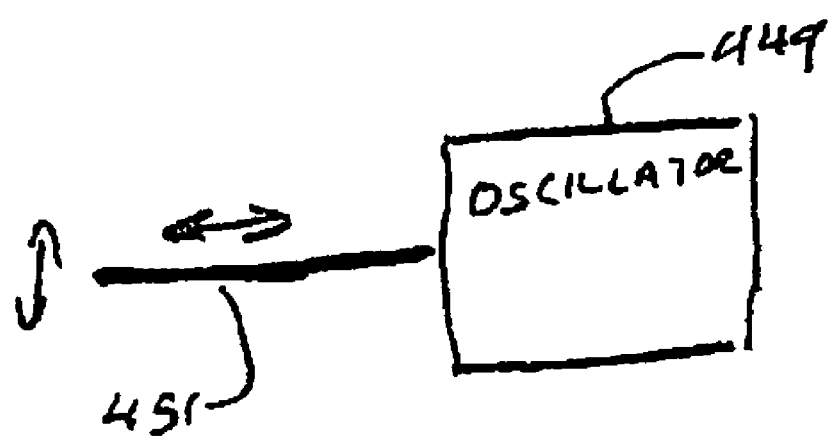
FIG. 4F shows a schematic oscillator for oscillating a blunt dissector, for instance, a wire.

The wire dissecting member may be oscillated using an oscillator appropriately coupled to the wire and along the axis of the wire. Some caution must be exercised using such an oscillation though, in that such an oscillation has a higher tendency to cut the cornea. I have found that a wire frequency in the range of 100-350 Hz., 200-325 Hz., perhaps 225-275 Hz., and perhaps 245-255 Hz. works quite well to raise the epithelium. The amplitude of these oscillations may be 1.5-4.5 mm, perhaps 2-3 mm, are quite suitable. FIG. 4F provides a schematic oscillator (449) coupled to a blunt dissecting member (451), wire or spatula (discussed below), suitable for oscillating the dissector in one or more directions.

An oscillation in which the tension of the wire is varied, e.g., 0 kpsi to 35 kpsi, perhaps 25 kpsi to 32.5 kpsi, often 25 kpsi to 30 kpsi. I have found these to be especially appropriate values when using about 0.002" stainless steel wire, but some level of experimentation is appropriate when designing these devices to meet the functional de-epithelization limitations recited here.

As noted elsewhere, the wire or wire structure may be actively rotated or allowed to rotate during the dissection step.

Although the procedure here is normally used to dissect a substantially intact sheet of the epithelium, i.e., the portion of the epithelium that passes to the anterior side of the dissector wire is continuous, the device may be used in less elegant ways. For instance, the dissector may be used to remove selected portions of that membrane. Indeed, when this device is used in conjunction with a LASEK procedure, the epithelium may be removed in the form of a soft flap allowing for ease of replacement or re-positioning once any corneal laser remodeling is completed. Some variations of the dissector may be used to form an epithelial pocket. Use of an ocular topography system such as that described in U.S. Pat. No. 5,777,719, a wavefront sensing system for measuring and correcting higher-order aberrations is contemplated in conjunction with some variations of my procedure.

A jig or form (470) suitable for variously locating the dissection wire accurately on the eye and limiting the movement of the dissector wire so to form a flap of epithelium, is found in FIGS. 5A-5E.

FIGS. 5A and 5B show perspective views of an example of the jig (470), with a section removed to depict underside details with respect to a typical eye (472). This example of the device uses a handle (474) having a vacuum lumen (476). The vacuum is applied to a sealing volume (478) having a pair of sealing ridges (480, 482) that contact the eye (474) and allow the jig (470) to grasp the eye (474) and immobilize jig (470) and eye (474) with respect to each other.

Figure 5C:
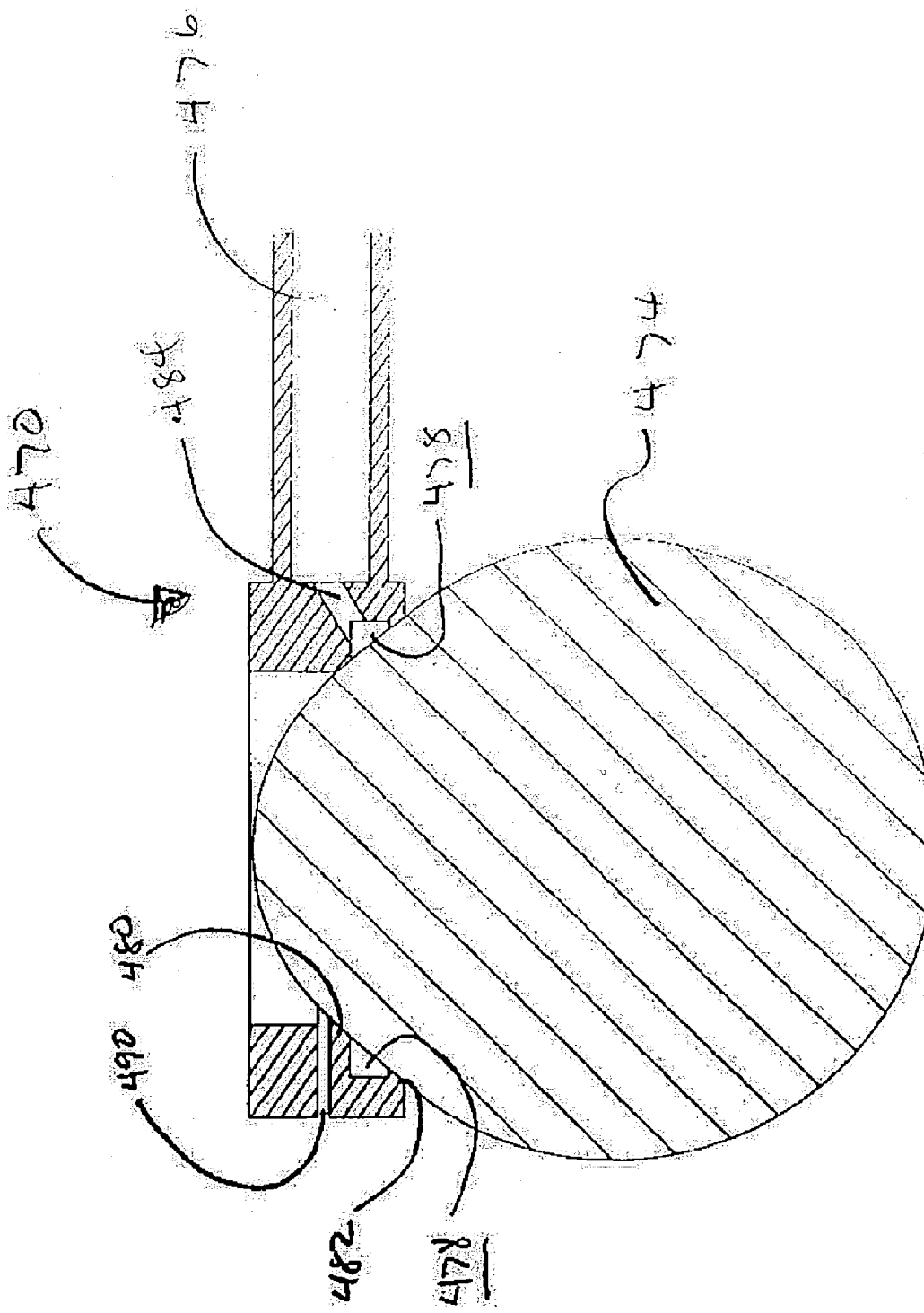
FIG. 5C shows a side-view, cutaway of the FIG. 5A jig situated on an eye.

FIG. 5C shows a side-view, cross-section of the jig (470) forming sealing volume (478) between sealing ridges (486, 482). The vacuum passageway (484) between the vacuum lumen (476) and the sealing volume (478) may also be seen. Clearly seen in FIG. 5C is the guide slot (490), a slot passing only partially around the jig (470). The guide slot (490) may also be seen in FIGS. 5A and 5B.

FIGS. 5D and 5E show the extent of the placement of the guide slot (490) in that it ends (492) near the handle (474). When a wire dissector is introduced into guide slot (490), it dissects the epithelium from a site in the epithelium near the site at which the wire enters, but since the wire can go no further than the ends (492) of the guide slot, it dissects only a flap of epithelium.

Figure 5F:
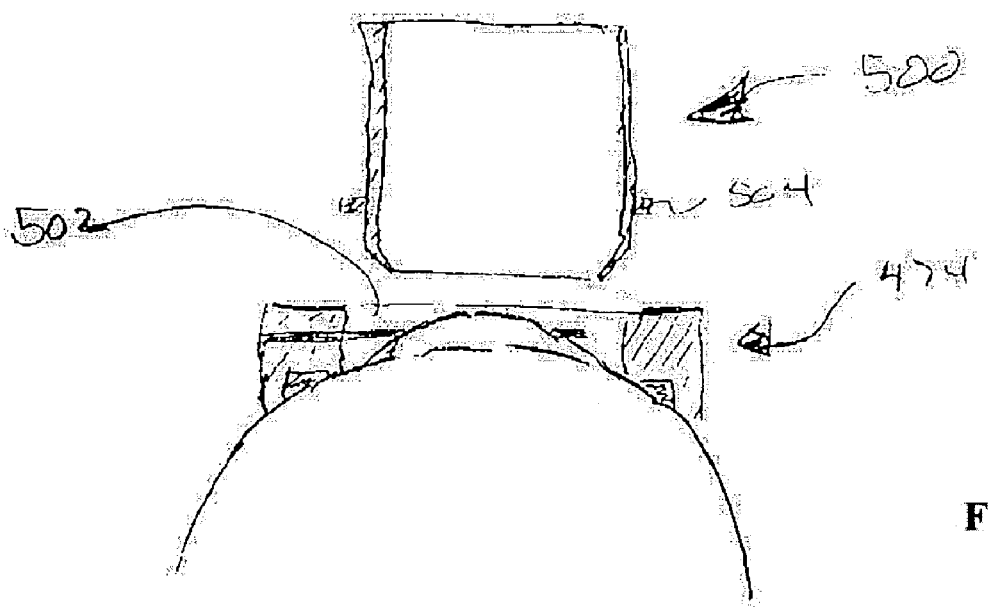
FIG. 5F shows the FIG. 5A jig and an epithelium scorer situated on an eye.

To control the shape of the dissected epithelium flap with even greater accuracy, a scoring tool (500) as shown in FIG. 5F may be used, perhaps in conjunction with a vacuum jig as shown in FIGS. 5A and 5B. The scoring tool (500) may be sized to fit within the upper aperture (502) of the jig (474): Appropriate stops (504) may be placed on the scoring tool (500) or on the jig (474) to limit the depth of the cut or "score" in the epithelium. The depth of the score should be (obviously) no greater than the thickness of that epithelial layer. Normally 10% to 90%, more often 30% to 70% at this depth is acceptable.

Finally, it may be desirable to heat the wire dissector a small amount, e.g., perhaps 1° to 5° C. above ambient or ocular temperature, to increase the ease with which the epithelium releases.

Figure 6A:
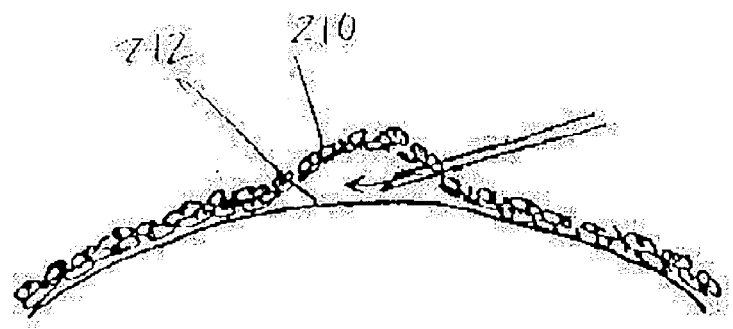
FIG. 6A is a side, cross-sectional view of a curved spatula lifting a portion of the epithelium by blunt dissection.

In another variation, FIG. 6A shows an epithelial delaminator including a blunt dissector that injects a fluid, a gel, or a gas between the corneal epithelium (210) and stroma (212). The fluid or gel may be injected using a needle (214) or cannula. Fluids that may be used for injection include saline solutions, e.g., saline solutions (such as 1M hypertonic saline), silicone-based compounds and solutions, detergent solutions, $CO_2$, $N_2$, and air. Oils, generally hydrophobic, e.g., mineral oils and other injectable carbon-based oils or silicone oils may be used. Upon injection, the fluid or gel bluntly dissects or separates the epithelium (210) from the stroma (212). If desired, the addition of pulsing, e.g.; oscillatory motion or ultrasonic motion, to the fluid may be provided to enhance epithelial delamination.

Figure 6B:
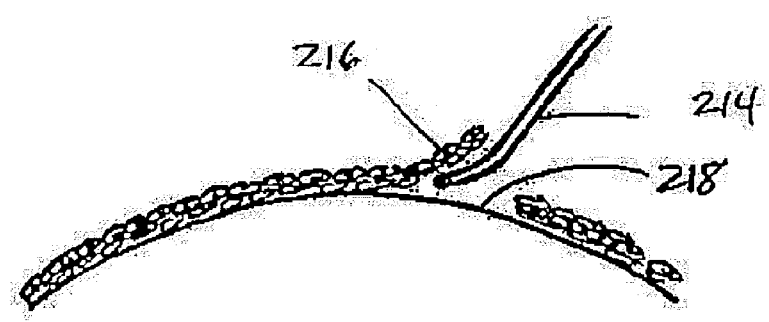
FIG. 6B is a side, cross-sectional view of an injected fluid or gel lifting a portion of the epithelium.
Figure 6C:
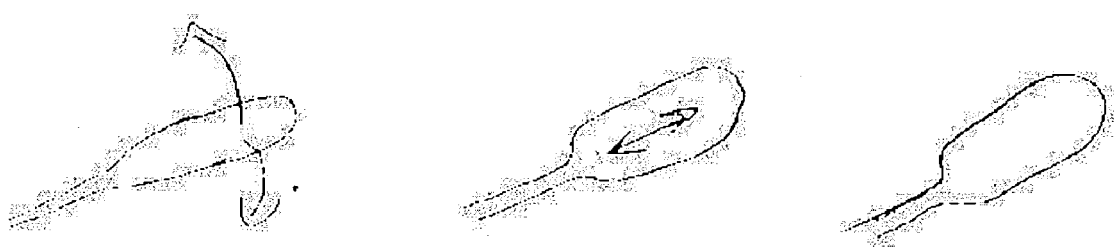
FIG. 6C shows a number of blunt dissectors and their potential movements during de-epithelialization.

In another variation of the blunt dissector, a solid instrument, e.g., a spatula or other mechanical dissector not supported on each side of a dissection zone in the epithelium, may be used as a blunt dissector that uses a separating force to dissect the epithelium from the corneal stroma. FIG. 6B shows a curved spatula (214) lifting a continuous layer of epithelium (216) off the corneal stroma. Other examples of the spatula variation of the dissector may have motions as shown in FIG. 6C, e.g., partial rotational (510), axial (512), and oscillatory (514).

Chemical Epithelial Delaminators

Figure 7A:
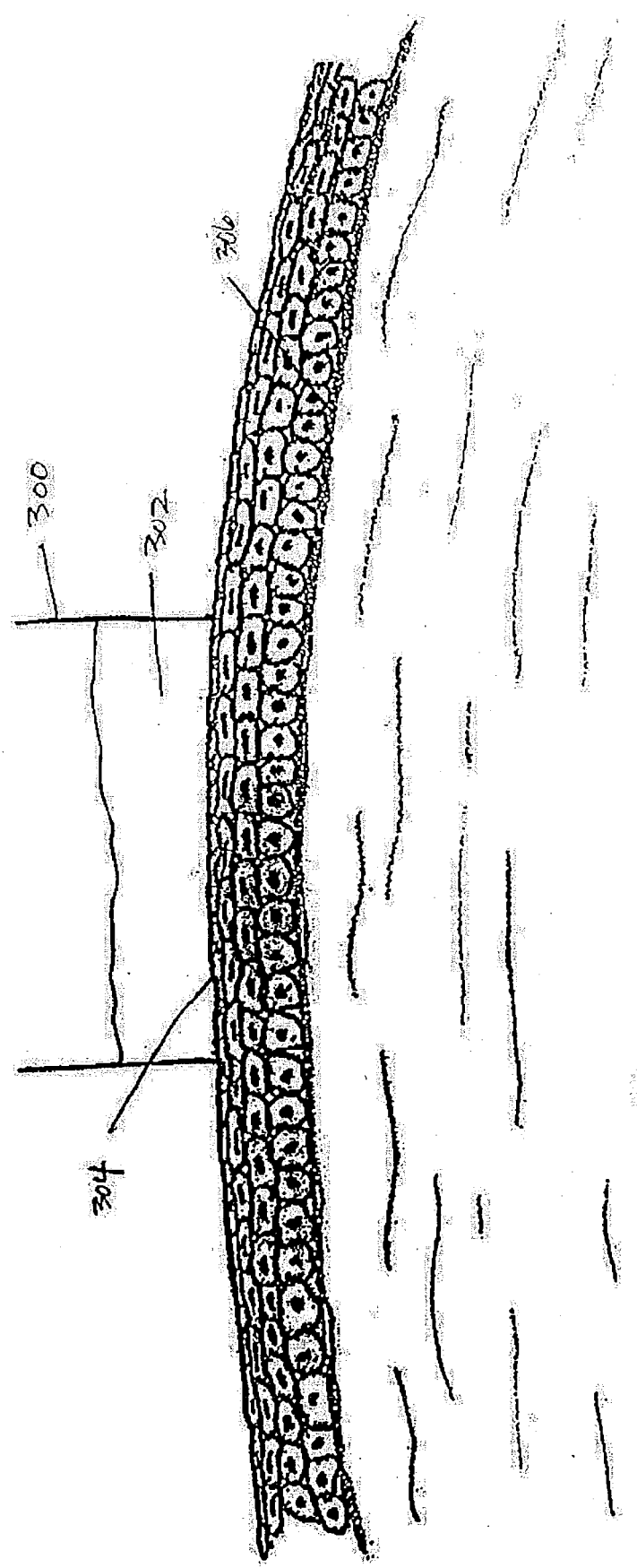
FIG. 7A shows a side, cross-sectional view of a well filled with a chemical composition for lifting the epithelium on a portion of the corneal epithelium.

LASEK procedures are often performed using a 20% ethanol in balanced salt solution to remove the overlying epithelium. Twenty percent ethanol is placed in a well on the eye and allowed to destroy the adherent function of the epithelium over a period of two to five minutes. However, application of a 20% ethanol solution kills a portion of epithelial cells, hindering the ability of the epithelium to be lifted in a continuous layer. In one embodiment of the present invention, as seen in FIG. 7A, the epithelial delaminator includes a well (300) filled with an ethanol solution (302) that has a lower percentage of ethanol (0.5% up to 15%) so that cell loss is minimized. Upon application of the ethanol solution (302) to the anterior surface of the eye, the epithelium (304) is lifted from the stromal surface (306) in a continuous layer.

Other chemical compositions may be included in chemical epithelial delaminators for application to the eye. The compositions may be aqueous solutions, gels, e.g., hydrogels, or solids. The compositions may be directly applied to the eye or applied after placement on an absorbent pad in an amount sufficient to lift the epithelium in a continuous layer. Any type of absorbent pad may be used, but typically, a gauze pad soaked with the chemical composition would be applied. FIG. 7B shows an absorbent pad containing a chemical composition for epithelial delamination (308) contacting the epithelium (310.

Preferred chemical compositions for epithelial delamination include vesicants such as 1M hypertonic saline, ethanol, cantharidin, and CEES. Diluents may also be added to the composition prior to eye application. A suitable diluent for cantharidin is acetone. A suitable diluent for CEES is water or humidified air. Typically, as with cantharidin and CEES, the compounds work by destroying the basal epithelial cells themselves, but do not harm the epithelial cells that reside above the basal epithelial layer. If 1M hypertonic saline is used, the basement membrane complex dissociates along the lamina lucida. Basal epithelial cells are generally not destroyed. Incubation of any epithelia in 1M hypertonic saline achieves a pure separation of epithelium from the underlying connective tissue.

In some instances it may be desirable to also apply heat to the anterior surface of the eye to speed up mechanical or chemical epithelial delamination. Referring back to FIG. 2A, suction apparatus (100) may include a port or groove (128) for entry of a heated fluid to warm the surface of the eye. Port or groove (128) may also provide for entry of an ophthalmologic instrument to assist in the delamination process.

The epithelial delaminating methods herein described may also be used in conjunction with corneal reshaping procedures or procedures that involve placement of ocular lens devices on the surface of the eye. Specifically, the disclosed procedure may be used to prepare an epithelial flap, often with an attached hinge. A suitable ocular lens may then be placed on the stromal surface and the epithelial flap replaced over the lens. One such suitable ocular lens device to be used with the present invention is described in Application No. PCT/US01/22633 which is herein incorporated by reference in its entirety.

Similarly, a corneal reshaping procedure may be performed and the corneal flap replaced.

Furthermore, use of a vibrating or oscillating force in conjunction with any of the epithelial delaminators described above may enhance epithelial delamination. Oscillatory force used in any of the above methods would accelerate delamination by stimulating the resonant frequency of molecules in the basement membrane which in and of itself would disrupt epithelial cell attachments.

EXAMPLE

A mechanical epithelial delamination was performed using a device similar to those shown in FIGS. 4A, 4B, 4C, 4D, and 4E, in that it had a yoke assembly with a yoke arms that drooped and included a dissecting wire having a diameter of 2 mil. (0.002 inch). The yoke was vibrated along the axis of the handle at about 250 Hz. A jig as shown in FIGS. 5A-5E was placed on the anterior surface of a freshly harvested pig eye (6 hours post-mortem) and vacuum was applied.

Figure 8A:
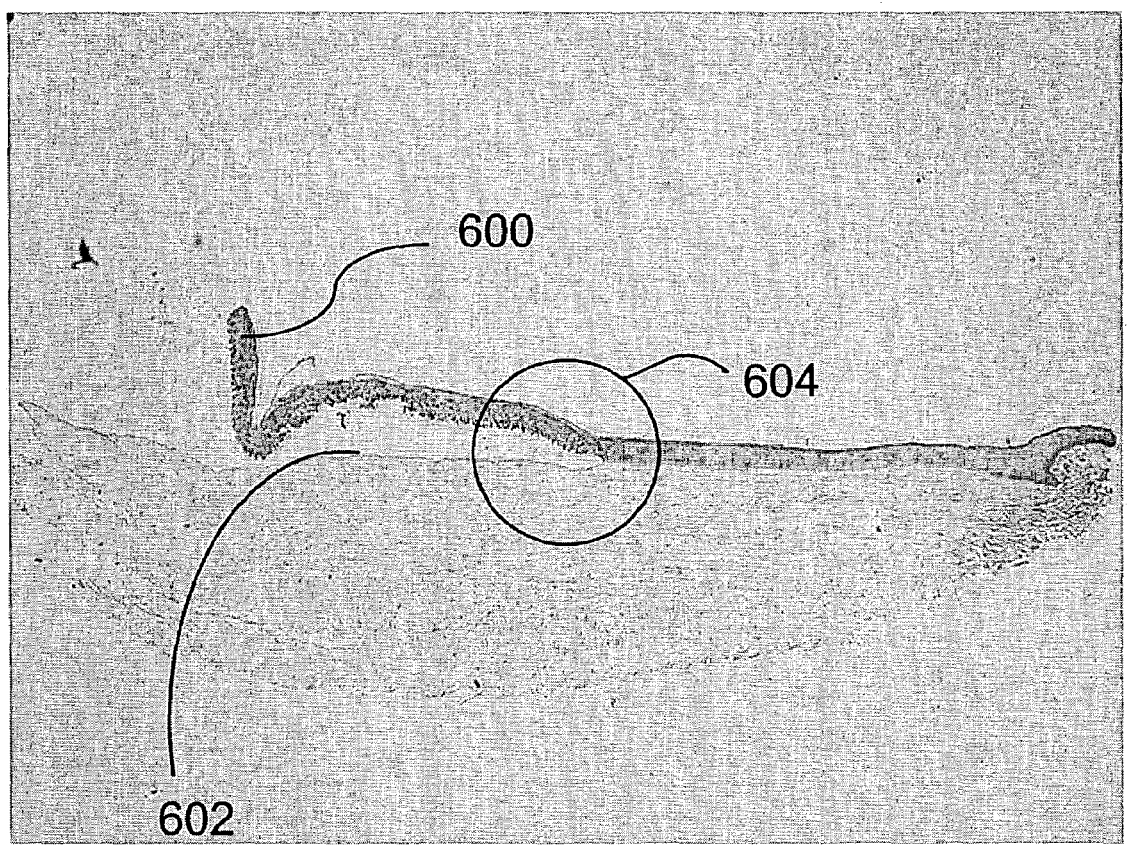
FIG. 8A shows the surface of the eye with lifted and separated epithelium and the stromal surface.
Figure 8B:
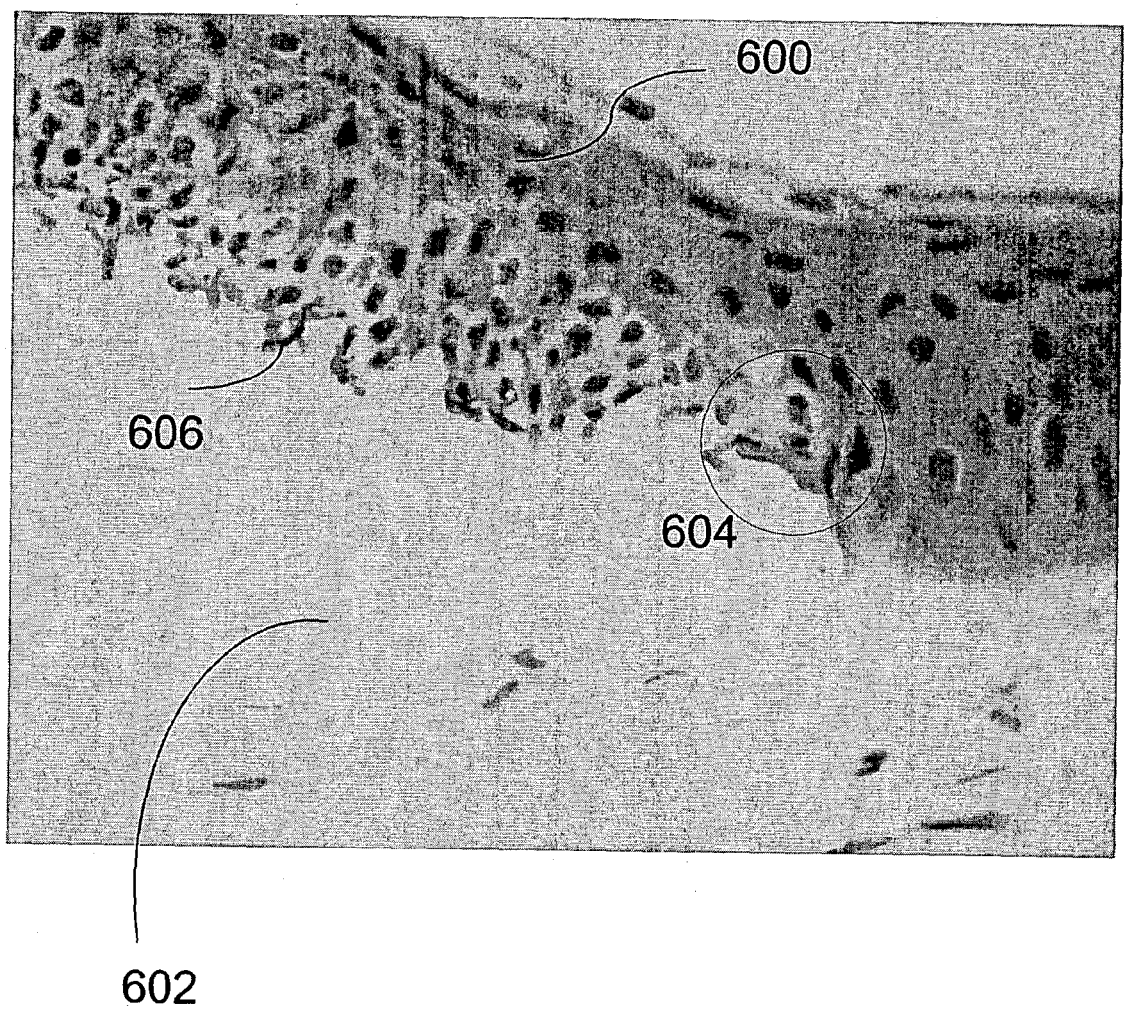
FIG. 8B shows a closer view of the separated epithelium.

The wire was passed through the jig beneath the epithelium and a flap of the epithelium was raised. Histological samples of the remaining corneal surface, the raised epithelium, and the limn where the "hinge" of the flap met the cornea were taken. FIG. 8A shows the dissected and raised epithelium (600), the cornea (602), and the junction (604) where the dissection was terminated. FIG. 8B shows, in higher magnification, the junction (604) and further displays the precision of the blunt mechanical dissection: there is an absence of visible corneal, stromal tissue on the basal cell layer (606) of the epithelium (600) and, similarly, there are no basal cells on the surface of the cornea (602).

Figure 8C:
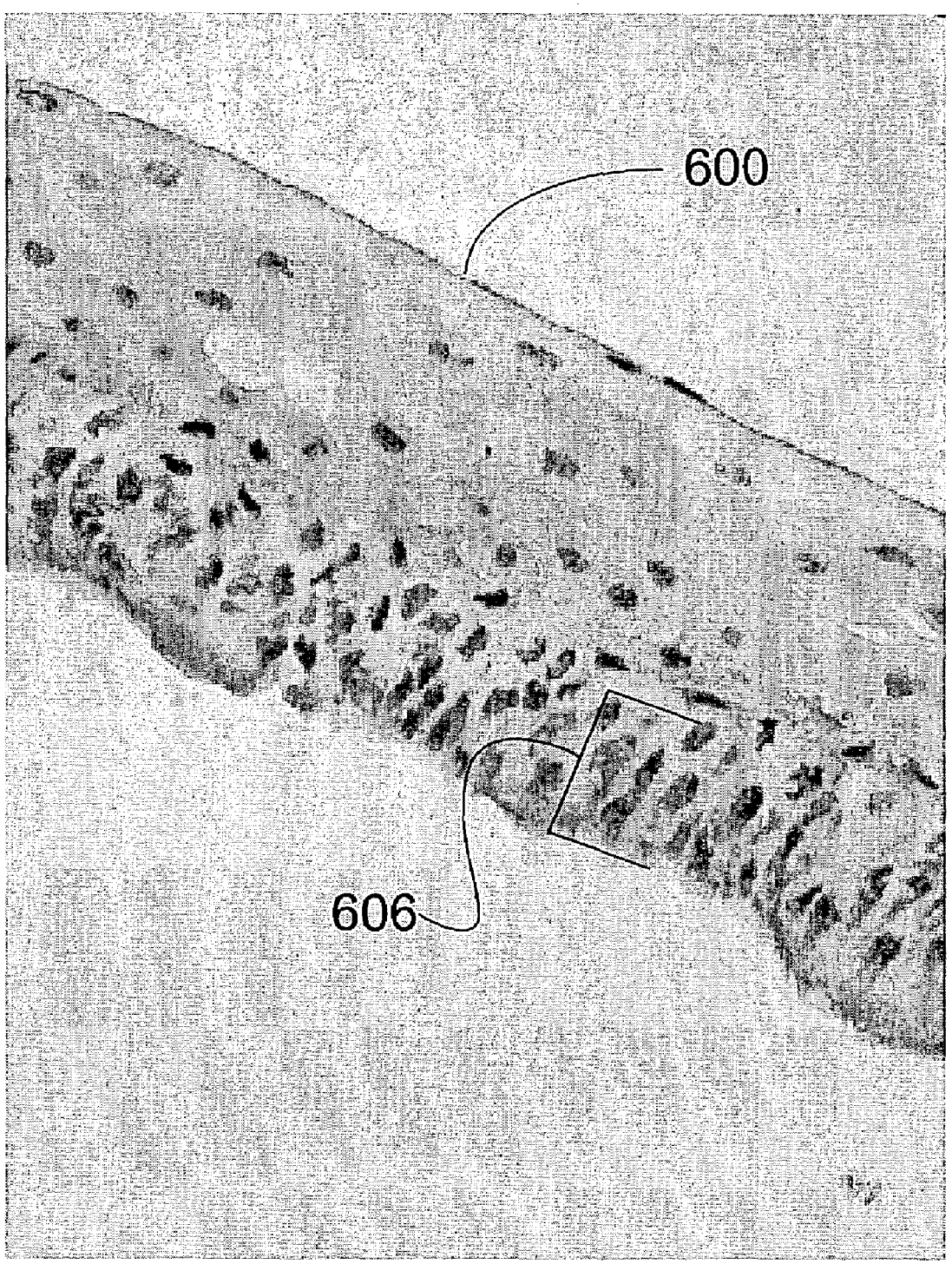
FIG. 8C shows a still closer view of the separated epithelium.

FIG. 8C shows (in still higher magnification) the dissected epithelium (600) and the basal cell layer (606). Again, even at this magnification, no stromal tissue is seen.

Figure 8D:
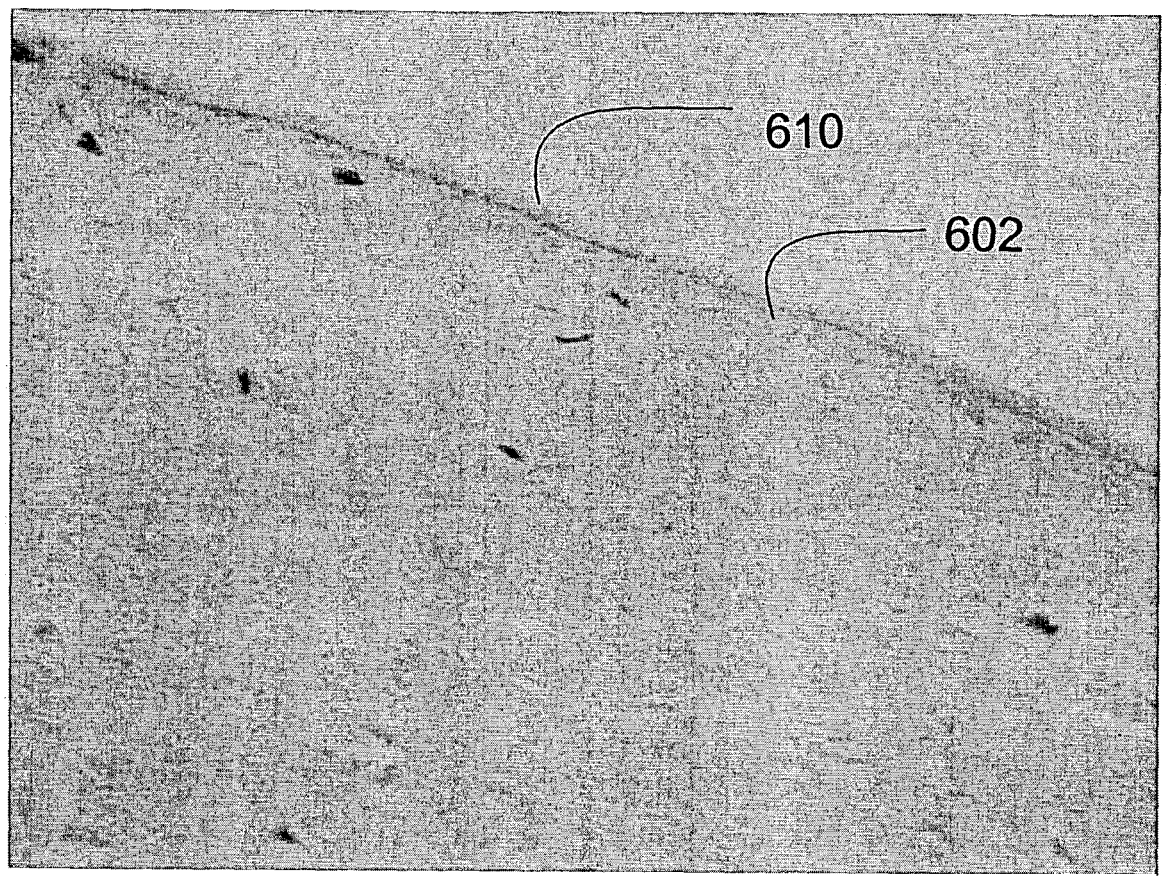
FIG. 8D shows a view of the remaining stromal surface of the eye.

FIG. 8D shows (in high magnification) the surface of the cornea (602) and Bowman's membrane (610). No epithelial cells are seen.

The structure and physiologic properties for my invention, as well as certain of the benefits particular to the specific variations of this epithelial delaminating device, have been described. This manner of describing the invention should not, however, be taken as limiting the scope of the invention in any way.

I claim as my invention:

1. A device for separating epithelium from an eye having a cornea with epithelium and a stroma, the device comprising an epithelial delaminator member configured to contact the stroma beneath the epithelium and thereby to apply a mechanical force beneath that epithelium to separate the epithelium from the stroma without cutting that stroma.

2. The device of claim 1 wherein the epithelial delaminator member is configured to produce a separated epithelium being substantially free of Collagen Type I and Collagen Type III.

3. The device of claim 1 wherein the epithelial delaminator member is configured to indent the stroma while applying the mechanical force beneath the epithelium.

4. The device of claim 1 wherein the epithelial delaminator member is configured to separate the epithelium in at least one continuous portion.

5. The device of claim 1 wherein the epithelial delaminator member is configured to separate the epithelium in one continuous portion.

6. The device of claim 1 wherein the epithelial delaminator member is configured to separate the epithelium and form an epithelial pocket.

7. The device of claim 6 wherein the epithelial delaminator member comprises a blunt dissector.

8. The device of claim 6 wherein the epithelial delaminator member comprises a spatula.

9. The device of claim 7 wherein the blunt dissector is configured to impart a shearing force.

10. The device of claim 7 wherein the blunt dissector is configured to impart an oscillating translational force.

11. The device of claim 6 further comprising, in combination, an implant configured to be placed on the stroma beneath the separated epithelium.

12. The device of claim 6 further comprising, in combination, an ocular lens configured to be placed on the stroma beneath the separated epithelium.

13. The device of claim 6 further comprising, in combination, an ocular lens comprising a synthetic polymer configured to be placed on the stroma beneath the separated epithelium.

14. The device of claim 1 wherein the epithelial delaminator member comprises a wire having a stiffness and size selected to separate the epithelium from the stroma.

15. The device of claim 14 wherein the wire has a cross section selected from the group consisting of round, square, oval, ellipsoid, rectangular, truncated oval, and bull-nosed.

16. The device of claim 14 wherein the wire has a length and a cross section that is not constant along that length.

17. The device of claim 14 wherein the wire has a prow positioned to lead a passage of the wire when passed beneath the epithelium.

18. The device of claim 14 wherein the wire is twisted along its length.

19. The device of claim 18 wherein the wire is helically twisted along its length.

20. The device of claim 18 wherein the wire is twisted non-uniformly along its length.

21. The device of claim 14 wherein the wire stiffness is selected at least partially by material selection of the wire.

22. The device of claim 14 wherein the wire stiffness is selected at least partially by adjusting the strain placed upon the wire.

23. The device of claim 14 further comprising a yoke supporting the wire.

24. The device of claim 23 wherein the yoke is configured to pass the wire beneath the epithelium at a direction of movement perpendicular to the wire.

25. The device of claim 23 wherein the yoke is configured to pass the wire beneath the epithelium at a direction of movement not perpendicular to the wire.

26. The device of claim 14 further comprising an oscillator configured to oscillate the wire.

27. The device of claim 26 where the oscillator is configured to oscillate the wire at a frequency between 100 and 350 Hz.

28. The device of claim 27 where the oscillator is configured to oscillate the wire at an amplitude between 2.0 and 3.0 mm.

29. The device of claim 27 wherein the oscillator is configured to oscillate the wire at a direction of movement perpendicular to the wire.

30. The device of claim 27 wherein the oscillator is configured to oscillate the wire at a direction of movement not perpendicular to the wire.

31. The device of claim 26 where the oscillator is configured to oscillate the wire at a frequency between 245 and 255 Hz.

32. The device of claim 26 where the oscillator is configured to oscillate the wire at an amplitude between 1.5 and 4.5 mm.

33. The device of claim 14 further comprising a suction apparatus comprising:
epithelial contact surfaces defining a suction chamber,
a slot for directing the wire to the epithelium, and
a vacuum source in vacuum communication with the suction chamber.

34. The device of claim 33 wherein the suction chamber comprises a volume between two epithelial contact surfaces.

35. The device of claim 33 wherein the contact surfaces are ring shaped.

36. The device of claim 33 wherein the suction apparatus further includes a port for entry of an ophthalmologic surgical instrument.

37. The device of claim 1 wherein the epithelial delaminator member is configured to roll as it contacts the stroma and separates the epithelium.

38. The device of claim 37 wherein the epithelial delaminator member is configured to roll passively as it contacts the stroma and separates the epithelium.

39. The device of claim 37 wherein the epithelial delaminator member is configured to roll actively as it contacts the stroma and separates the epithelium.

40. The device of claim 37 wherein the rollable epithelial delaminator member comprises a wire structure comprising at least two wires and the structure selected to separate the epithelium from the stroma.

41. The device of claim 40 wherein the wire structure has a stiffness and size selected to separate the epithelium from the stroma.

42. The device of claim 40 wherein the wire structure comprises more than two wires.

43. The device of claim 40 wherein the wire structure comprises wires laid side-by-side and twisted together along its length.

44. The device of claim 40 wherein the wire structure is helically twisted along its length.

45. The device of claim 40 wherein the wire structure is twisted non-uniformly along its length.

46. The device of claim 40 wherein the wire structure comprises braided wires.

47. The device of claim 37 wherein the rollable epithelial delaminator member comprises a wire structure comprising at least one wire having a non-smooth surface and the surface suitable for separating the epithelium from the stroma.

48. The device of claim 37 wherein the rollable epithelial delaminator member comprises a wire structure comprising at least one wire having a roughened surface suitable for separating the epithelium from the stroma.

49. The device of claim 1 wherein the epithelial delaminator member comprises a blunt dissector.

50. The device of claim 49 wherein the blunt dissector is configured to impart a shearing force.

51. The device of claim 49 wherein the blunt dissector is configured to impart an oscillating translational force.

52. The device of claim 1 wherein the epithelial delaminator member comprises a spatula.

53. The device of claim 1 further comprising, in combination, an implant configured to be placed on the stroma beneath the separated epithelium.

54. The device of claim 1 further comprising, in combination, an ocular lens configured to be placed on the stroma beneath the separated epithelium.

55. The device of claim 1 further comprising, in combination, an ocular lens comprising a synthetic polymer configured to be placed on the stroma beneath the separated epithelium.

56. A device for lifting epithelium from an eye having a cornea with an anterior surface comprising an epithelial delaminator configured to apply a mechanical force to the anterior surface to lift the epithelium in a continuous layer.

57. The device of claim 56 wherein the epithelial delaminator comprises a
suction apparatus comprising:
a suction chamber having an epithelial contact surface and a vacuum source,
wherein the suction chamber and the vacuum source are in vacuum communication.

58. The device of claim 57 wherein the suction chamber comprises a wall.

59. The device of claim 57 wherein the suction chamber is a hemispherical cup.

60. The device of claim 59 wherein the cup is transparent.

61. The device of claim 59 wherein the cup is comprised of a deformable material.

62. The device of claim 57 wherein the contact surface is ring shaped.

63. The device of claim 62 wherein the ring shaped contact surface is comprised of a material selected from the group consisting of a metal, a polymer, and an elastomer.

64. The device of claim 57 wherein the suction chamber includes a port or a groove for entry of a fluid.

65. The device of claim 64 wherein the epithelial delaminator further comprises a fluid.

66. The device of claim 65 wherein the fluid comprises hypertonic saline.

67. The device of claim 57 wherein the suction chamber includes a port or a groove for entry of an ophthalmological surgical instrument.

68. The device of claim 57 wherein the vacuum source is a manual pump.

69. The device of claim 57 wherein the vacuum source is a motorized pump.

70. The device of claim 57 further comprising a pressure gauge.

71. The device of claim 57 wherein the vacuum source is a syringe.

72. The device of claim 56 wherein the delaminator is a blunt dissector.

73. The device of claim 72 wherein the delaminator comprises a rotating wire.

74. The device of claim 72 wherein the delaminator comprises a vibrating wire.

75. The device of claim 72 wherein the delaminator comprises a curved spatula.

76. The device of claim 72 wherein the blunt dissector is configured to impart a shearing force.

77. The device of claim 56 wherein the epithelial delaminator is configured to apply the force by injecting a fluid between the epithelium and the anterior surface.

78. The device of claim 77 wherein the epithelial delaminator further comprises a fluid.

79. The device of claim 78 wherein the fluid comprises hypertonic saline.

80. The device of claim 78 wherein the fluid comprises a silicone solution.

81. The device of claim 77 wherein the fluid is air.

82. The device of claim 56 wherein the epithelial delaminator is configured to apply the force by injecting a gel between the epithelium and the anterior surface.

* * * * *